United States Patent
Gnahoui-David et al.

(10) Patent No.: US 9,585,949 B2
(45) Date of Patent: Mar. 7, 2017

(54) USE OF ATTENUATED STRAINS OF PARASITES FOR THE PREVENTION OR TREATMENT OF PATHOLOGIES ASSOCIATES WITH AN APICOMPLEXAN

(71) Applicants: VITAMFERO, Tours (FR); INSTITUT NATIONAL DE LA RECHERCHE AGRONOMIQUE, Paris Cedex (FR); UNIVERSITE FRANCOIS RABELAIS DE TOURS, Tours Cedex (FR)

(72) Inventors: Audrey Gnahoui-David, Tours (FR); Fabrice Laurent, Tours (FR); Marie-Noelle Mevelec, Tours (FR); Edouard Seche, Tours (FR)

(73) Assignees: VITAMFERO, Tours (FR); INSTITUT NATIONAL DE LA RECHERCHE AGRONOMIQUE, Paris (FR); UNIVERSITE FRANCOIS RABELAIS DE TOURS, Tours (FR)

( * ) Notice: Subject to any disclaimer, the term of this patent is extended or adjusted under 35 U.S.C. 154(b) by 0 days.

(21) Appl. No.: 15/016,189

(22) Filed: Feb. 4, 2016

(65) Prior Publication Data

US 2016/0166662 A1 Jun. 16, 2016

Related U.S. Application Data

(62) Division of application No. 14/418,984, filed as application No. PCT/FR2013/051876 on Aug. 2, 2013, now abandoned.

(51) Int. Cl.
*A61K 39/002* (2006.01)
*A61K 39/012* (2006.01)
*A61K 39/39* (2006.01)
*A61K 39/00* (2006.01)

(52) U.S. Cl.
CPC .......... *A61K 39/002* (2013.01); *A61K 39/012* (2013.01); *A61K 39/39* (2013.01); *A61K 2039/522* (2013.01); *A61K 2039/55* (2013.01); *A61K 2039/552* (2013.01); *A61K 2039/57* (2013.01); *A61K 2039/572* (2013.01); *A61K 2039/575* (2013.01); *A61K 2039/58* (2013.01)

(58) Field of Classification Search
CPC .................................................... A61K 39/002
See application file for complete search history.

(56) References Cited

FOREIGN PATENT DOCUMENTS

WO 2011011725 1/2015

OTHER PUBLICATIONS

Penrete-Vargas et al., "Protection against Lethal Neospora caninum Infection in Mice Induced by Heterologous Vaccination with a mic3 Knockout Toxoplasma gondii Strain", Infection and Immunity, 2010, vol. 78, No. 2, pp. 651-660.
International Search Report, dated Jun. 5, 2014, from corresponding PCT application.

*Primary Examiner* — Albert Navarro
*Assistant Examiner* — Mark Navarro
(74) *Attorney, Agent, or Firm* — Young & Thompson

(57) ABSTRACT

Strains of Sarcocystidae selected from *Toxoplasma* spp or *Neospora* spp isolated from their natural environment and having an immunostimulant effect, for the use thereof in the prevention or the treatment, in a mammal, of a pathology associated with an apicomplexan of the family Cryptosporidiidae.

15 Claims, 19 Drawing Sheets

FIGURE 2-A
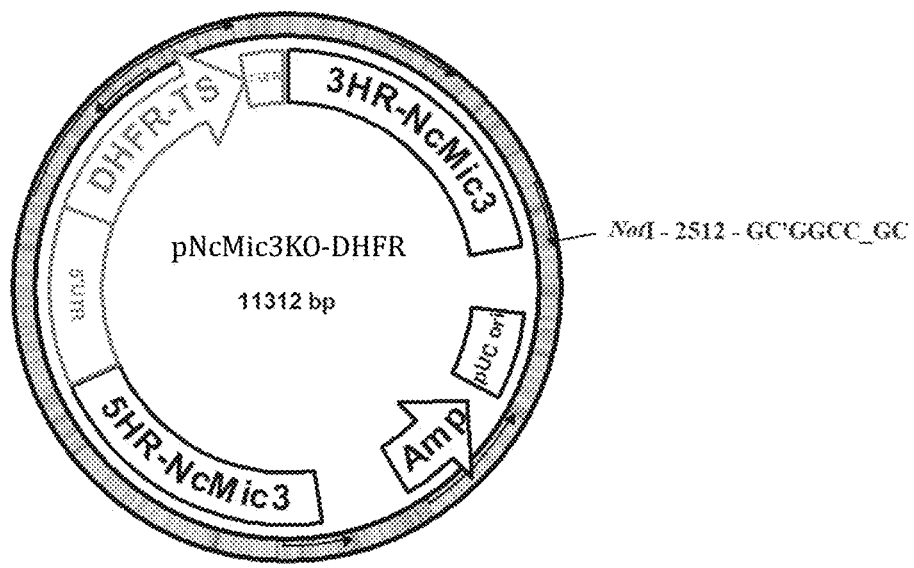
FIGURE 2-B
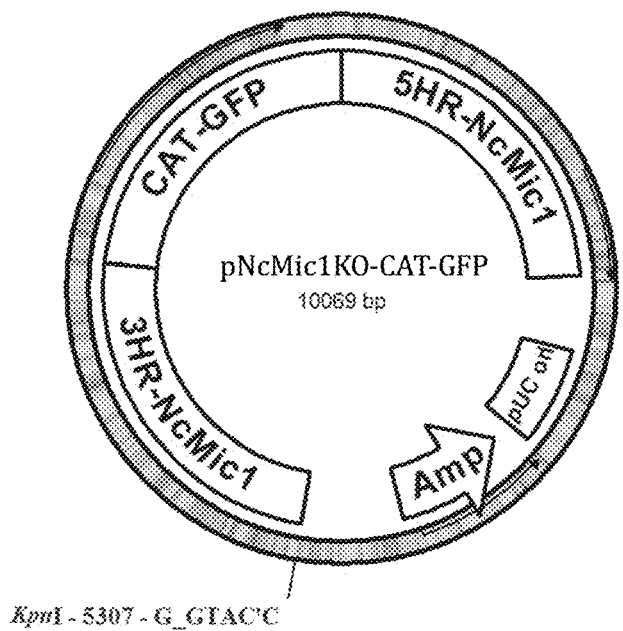

FIGURE 3-A
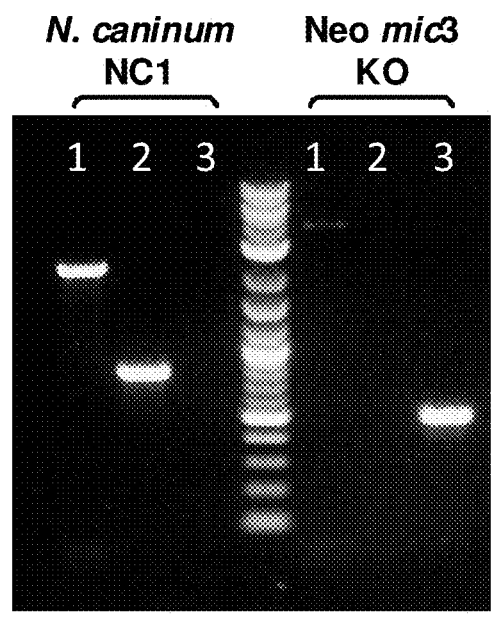
FIGURE 3-B
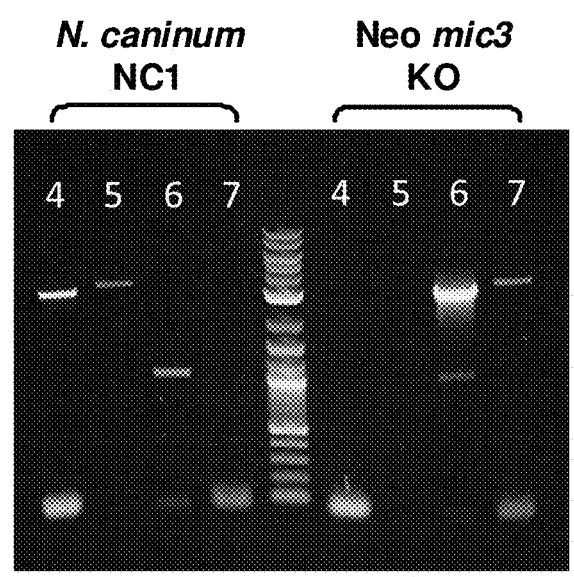

FIGURE 4-A
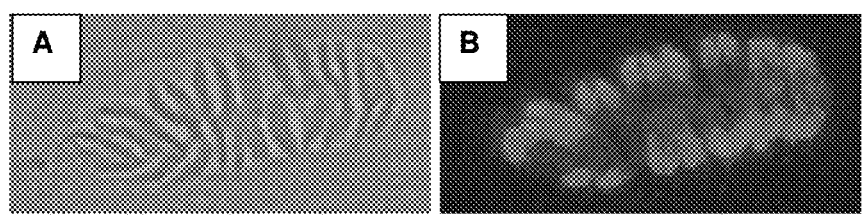
FIGURE 4-B
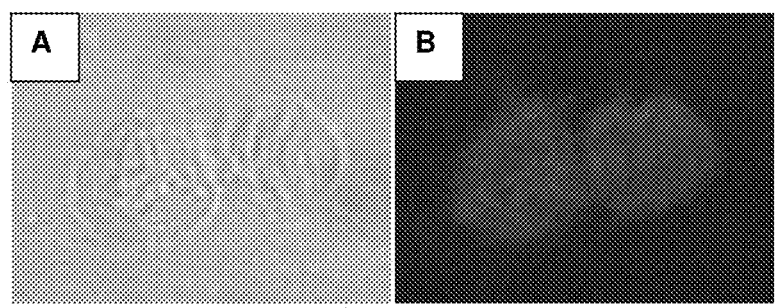

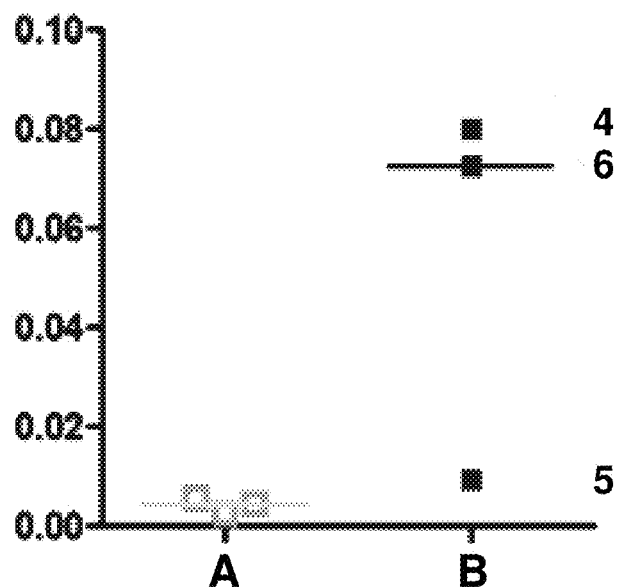
FIGURE 8-A
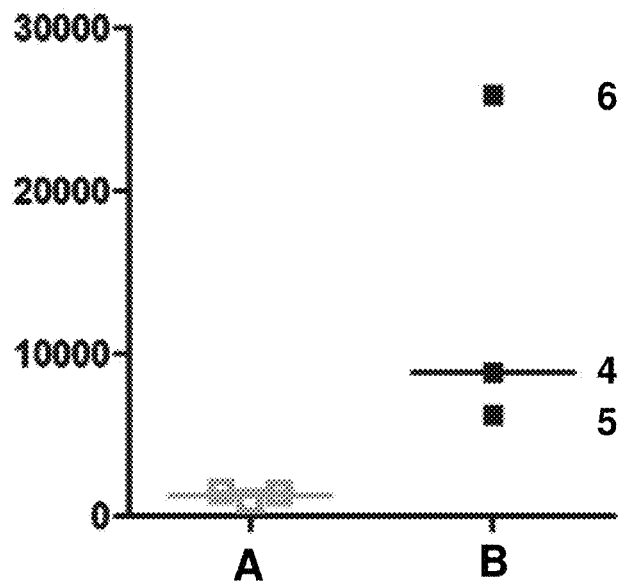
FIGURE 8-B

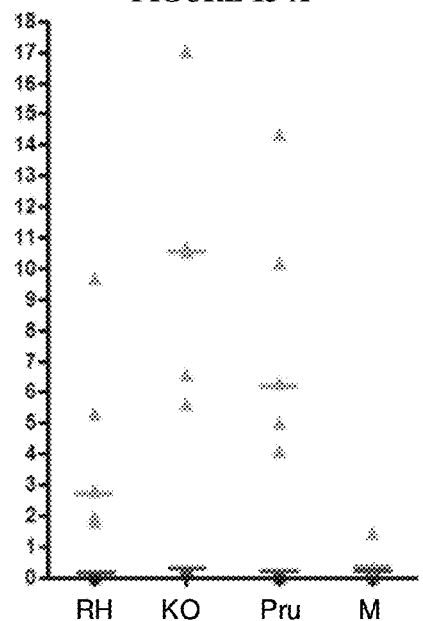
FIGURE 13-A
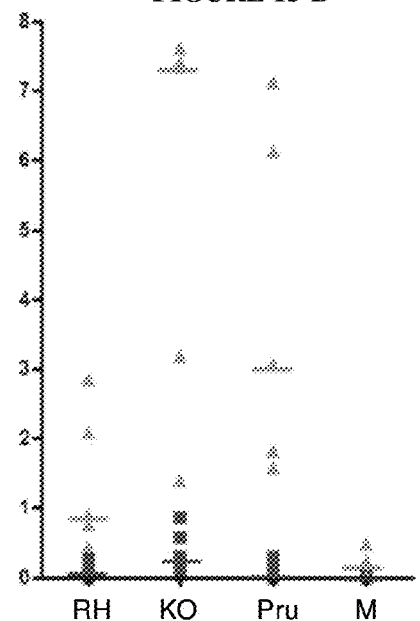
FIGURE 13-B
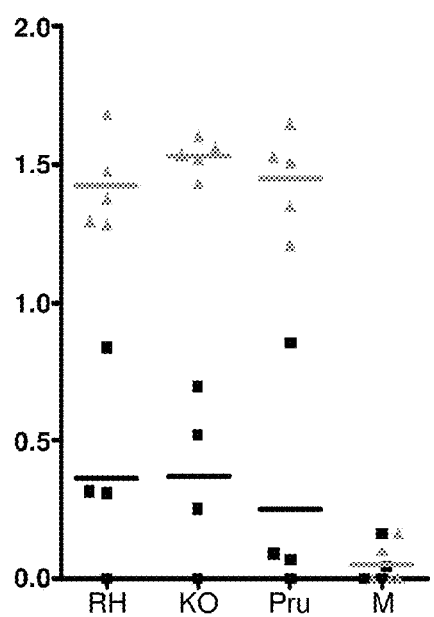
FIGURE 13-C

SEQUENCE LISTING

```
<160> NUMBER OF SEQ ID NOS: 38

<210> SEQ ID NO 1
<211> LENGTH: 34
<212> TYPE: DNA
<213> ORGANISM: Artificial Sequence
<220> FEATURE:
<223> OTHER INFORMATION: 5 HR NCmic3 F KpnI

<400> SEQUENCE: 1
cgcggtaccc atgtgaatat gctttaaccg tgac                                  34

<210> SEQ ID NO 2
<211> LENGTH: 34
<212> TYPE: DNA
<213> ORGANISM: Artificial Sequence
<220> FEATURE:
<223> OTHER INFORMATION: 5 HR NCmic3 R ClaI

<400> SEQUENCE: 2
cgcatcgatg agctataacc cttggaaatg actc                                  34
```

<210> SEQ ID NO 3
<211> LENGTH: 31
<212> TYPE: DNA
<213> ORGANISM: Artificial Sequence
<220> FEATURE:
<223> OTHER INFORMATION: 3 HR NCmic3 F XbaI

<400> SEQUENCE: 3
cgctctagac atgctgatga agaagggaag t                              31

<210> SEQ ID NO 4
<211> LENGTH: 34
<212> TYPE: DNA
<213> ORGANISM: Artificial Sequence
<220> FEATURE:
<223> OTHER INFORMATION: 3 HR NCmic3 R NotI

<400> SEQUENCE: 4
cgcgcggccg ctctctcctg aagtcttcga gacc                           34

<210> SEQ ID NO 5
<211> LENGTH: 25
<212> TYPE: DNA
<213> ORGANISM: Artificial Sequence
<220> FEATURE:
<223> OTHER INFORMATION: HR NCmic3 F

<400> SEQUENCE: 5
gtcatcgacc gccggaacta gtagt                                     25

<210> SEQ ID NO 6
<211> LENGTH: 26
<212> TYPE: DNA
<213> ORGANISM: Artificial Sequence
<220> FEATURE:
<223> OTHER INFORMATION: HR NCmic3 R

<400> SEQUENCE: 6
gcagaggttc tgcgtatcta acacgg                                    26

<210> SEQ ID NO 7
<211> LENGTH: 21
<212> TYPE: DNA
<213> ORGANISM: Artificial Sequence
<220> FEATURE:
<223> OTHER INFORMATION: ORF NCmic3 F

<400> SEQUENCE: 7
tttcccttct aaacacagtc g                                         21

<210> SEQ ID NO 8
<211> LENGTH: 22
<212> TYPE: DNA
<213> ORGANISM: Artificial Sequence
<220> FEATURE:
<223> OTHER INFORMATION: ORF NCmic3 R

<400> SEQUENCE: 8
ccttcagtgg ttctccatga gt                                        22

<210> SEQ ID NO 9
<211> LENGTH: 20
<212> TYPE: DNA
<213> ORGANISM: Artificial Sequence
<220> FEATURE:
<223> OTHER INFORMATION: ORF DHFR F

<400> SEQUENCE: 9
ccttctcaga caacggggta                                         20

<210> SEQ ID NO 10
<211> LENGTH: 20
<212> TYPE: DNA
<213> ORGANISM: Artificial Sequence
<220> FEATURE:
<223> OTHER INFORMATION: ORF DHFR R

<400> SEQUENCE: 10
agatcttcac gcccttctca                                         20

<210> SEQ ID NO 11
<211> LENGTH: 24
<212> TYPE: DNA
<213> ORGANISM: Artificial Sequence
<220> FEATURE:
<223> OTHER INFORMATION: Integ NCmic3 F

<400> SEQUENCE: 11
gaaagtgtca gtggtagaga ctgc                                    24

<210> SEQ ID NO 12
<211> LENGTH: 27
<212> TYPE: DNA
<213> ORGANISM: Artificial Sequence
<220> FEATURE:
<223> OTHER INFORMATION: ORF NCmic3 R2

<400> SEQUENCE: 12
ccttcactcg agatcgcgca aatgagc                                 27

<210> SEQ ID NO 13
<211> LENGTH: 23
<212> TYPE: DNA
<213> ORGANISM: Artificial Sequence
<220> FEATURE:
<223> OTHER INFORMATION: ORF DHFR R2

<400> SEQUENCE: 13
ggacctctgt acgagacatg ccg                                     23

<210> SEQ ID NO 14
<211> LENGTH: 24
<212> TYPE: DNA
<213> ORGANISM: Artificial Sequence
<220> FEATURE:
<223> OTHER INFORMATION: Integ NCmic3 R

<400> SEQUENCE: 14
tgtttacagg tgatccagaa aagg                                    24

<210> SEQ ID NO 15
<211> LENGTH: 20
<212> TYPE: DNA
<213> ORGANISM: Artificial Sequence
<220> FEATURE:
<223> OTHER INFORMATION: ORF NCmic3 F2

<400> SEQUENCE: 15
gaattttggg acaggggaat                                         20

<210> SEQ ID NO 16

<211> LENGTH: 25
<212> TYPE: DNA
<213> ORGANISM: Artificial Sequence
<220> FEATURE:
<223> OTHER INFORMATION: ORF DHFR F2

<400> SEQUENCE: 16
gtctctcgtt ttcctctctt ttcgg                                    25

<210> SEQ ID NO 17
<211> LENGTH: 33
<212> TYPE: DNA
<213> ORGANISM: Artificial Sequence
<220> FEATURE:
<223> OTHER INFORMATION: 3 HR NCmic1 F KpnI

<400> SEQUENCE: 17
cgcggtacca ggcagaagta aagaaggttc ctc                           33

<210> SEQ ID NO 18
<211> LENGTH: 30
<212> TYPE: DNA
<213> ORGANISM: Artificial Sequence
<220> FEATURE:
<223> OTHER INFORMATION: 3 HR NCmic1 R HindIII

<400> SEQUENCE: 18
cgcaagcttt gatcacgcaa gaaaagaagc                               30

<210> SEQ ID NO 19
<211> LENGTH: 32
<212> TYPE: DNA
<213> ORGANISM: Artificial Sequence
<220> FEATURE:
<223> OTHER INFORMATION: 5 HR NCmic1 F BamHI

<400> SEQUENCE: 19
cgcggatccc atttgtagat acggttgcac ac                            32

<210> SEQ ID NO 20
<211> LENGTH: 33
<212> TYPE: DNA
<213> ORGANISM: Artificial Sequence
<220> FEATURE:
<223> OTHER INFORMATION: 5 HR NCmic1 R NotI

<400> SEQUENCE: 20
cgcgcggccg cacattcaga cggcagaact ctg                           33

<210> SEQ ID NO 21
<211> LENGTH: 20
<212> TYPE: DNA
<213> ORGANISM: Artificial Sequence
<220> FEATURE:
<223> OTHER INFORMATION: Integ NCmic1 F

<400> SEQUENCE: 21
ccgagcaagt tagcaagtcc                                          20

<210> SEQ ID NO 22
<211> LENGTH: 20
<212> TYPE: DNA
<213> ORGANISM: Artificial Sequence
<220> FEATURE:
<223> OTHER INFORMATION: ORF CATGFP R

<400> SEQUENCE: 22
ccgtttggtg gatgtcttct                                            20

<210> SEQ ID NO 23
<211> LENGTH: 20
<212> TYPE: DNA
<213> ORGANISM: Artificial Sequence
<220> FEATURE:
<223> OTHER INFORMATION: ORF CATGFP F

<400> SEQUENCE: 23
gcatcgactt caaggaggac                                            20

<210> SEQ ID NO 24
<211> LENGTH: 20
<212> TYPE: DNA
<213> ORGANISM: Artificial Sequence
<220> FEATURE:
<223> OTHER INFORMATION: Integ NCmic1 R

<400> SEQUENCE: 24
cttgtccgtc acatcgtttg                                            20

<210> SEQ ID NO 25
<211> LENGTH: 20
<212> TYPE: DNA
<213> ORGANISM: Artificial Sequence
<220> FEATURE:
<223> OTHER INFORMATION: ORF NCmic1 R

<400> SEQUENCE: 25
ttctccaggc actcacctct                                            20

<210> SEQ ID NO 26
<211> LENGTH: 20
<212> TYPE: DNA
<213> ORGANISM: Artificial Sequence
<220> FEATURE:
<223> OTHER INFORMATION: ORF NCmic1 F

<400> SEQUENCE: 26
agcttccaac aacgagagga                                            20

<210> SEQ ID NO 27
<211> LENGTH: 20
<212> TYPE: DNA
<213> ORGANISM: Artificial Sequence
<220> FEATURE:
<223> OTHER INFORMATION: ORF NCmic1 F2

<400> SEQUENCE: 27
cccaggatat cgtttgttgc                                            20

<210> SEQ ID NO 28
<211> LENGTH: 20
<212> TYPE: DNA
<213> ORGANISM: Artificial Sequence
<220> FEATURE:
<223> OTHER INFORMATION: ORF NCmic1 R2

<400> SEQUENCE: 28
cttctgatgc acggaactga                                            20

<210> SEQ ID NO 29
<211> LENGTH: 20
<212> TYPE: DNA

<213> ORGANISM: Artificial Sequence
<220> FEATURE:
<223> OTHER INFORMATION: ORF CATGFP F2

<400> SEQUENCE: 29
cctgaagttc atctgcacca                    20

<210> SEQ ID NO 30
<211> LENGTH: 20
<212> TYPE: DNA
<213> ORGANISM: Artificial Sequence
<220> FEATURE:
<223> OTHER INFORMATION: ORFCATGFP R2

<400> SEQUENCE: 30
gtagtggttg tcgggcagca                    20

<210> SEQ ID NO 31
<211> LENGTH: 21
<212> TYPE: DNA
<213> ORGANISM: Artificial Sequence
<220> FEATURE:
<223> OTHER INFORMATION: IL12 F

<400> SEQUENCE: 31
ctcacatctg ctgctccaca a                  21

<210> SEQ ID NO 32
<211> LENGTH: 21
<212> TYPE: DNA
<213> ORGANISM: Artificial Sequence
<220> FEATURE:
<223> OTHER INFORMATION: IL12 R

<400> SEQUENCE: 32
gacgccattc cacatgtcac t                  21

<210> SEQ ID NO 33
<211> LENGTH: 22
<212> TYPE: DNA
<213> ORGANISM: Artificial Sequence
<220> FEATURE:
<223> OTHER INFORMATION: IFN gamma F

<400> SEQUENCE: 33
tcttcttgga tatctggagg aa                 22

<210> SEQ ID NO 34
<211> LENGTH: 23
<212> TYPE: DNA
<213> ORGANISM: Artificial Sequence
<220> FEATURE:
<223> OTHER INFORMATION: IFN gamma R

<400> SEQUENCE: 34
agctcattga atgcttggcg ctg                23

<210> SEQ ID NO 35
<211> LENGTH: 22
<212> TYPE: DNA
<213> ORGANISM: Artificial Sequence
<220> FEATURE:
<223> OTHER INFORMATION: HPRT F

<400> SEQUENCE: 35
ggatacaggc cagactttgt tg                 22

```
<210> SEQ ID NO 36
<211> LENGTH: 20
<212> TYPE: DNA
<213> ORGANISM: Artificial Sequence
<220> FEATURE:
<223> OTHER INFORMATION: HPRT R

<400> SEQUENCE: 36
gagggtaggc tggcctatag                                                    20

<210> SEQ ID NO 37
<211> LENGTH: 25
<212> TYPE: DNA
<213> ORGANISM: Artificial Sequence
<220> FEATURE:
<223> OTHER INFORMATION: SAG-1 F

<400> SEQUENCE: 37
ctgcaccact tcattatttc ttctg                                              25

<210> SEQ ID NO 38
<211> LENGTH: 19
<212> TYPE: DNA
<213> ORGANISM: Artificial Sequence
<220> FEATURE:
<223> OTHER INFORMATION: SAG-1 R

<400> SEQUENCE: 38
actcacgcga cacaagctg                                                     19
```

USE OF ATTENUATED STRAINS OF PARASITES FOR THE PREVENTION OR TREATMENT OF PATHOLOGIES ASSOCIATES WITH AN APICOMPLEXAN

The present invention relates to the use of attenuated strains of parasites for preventing or treating pathologies associated with an apicomplexan.

The Apicomplexa are predominantly obligate intracellular parasites that have a life cycle that may involve several hosts. The phylum of these parasites is subdivided into several families.

*Toxoplasma gondii* (*T. gondii*) belongs to the Sarcocystidae family. This protozoon exists in three infectious forms which vary depending on the host and the infectious stage:
- tachyzoite: the infectious proliferative form which multiplies asexually in the cells of the intermediate hosts (i.e. all homeotherms) and definitive hosts (i.e. felids and the cat in particular),
- bradyzoite: slowly dividing form with low level of metabolism of the parasite contained in cysts,
- sporozoite: the form contained in the oocysts, which results from the sexual multiplication of the parasite in the intestine of the definitive hosts (i.e. cat and other felids).

The cat, the definitive host of the parasite, becomes infected by ingesting parasitized prey containing cysts (or tachyzoites if the animal is in the acute phase of toxoplasmosis), or by ingestion of oocysts. After sexual multiplication in the intestine of the felids, via gametocytes, the oocysts are disseminated in the environment. These oocysts sporulate in the external environment and they remain pathogenic for at least a year. After ingestion of oocysts, the released sporozoites infect the enterocytes of the definitive or intermediate host and undergo transformation to tachyzoites, which are disseminated in the organism. Under the pressure of the immune system, the tachyzoites become encysted with preferential tropism for the central nervous system, the retina or the muscles. Ingestion of encysted tissues is the second commonest cause of contamination of the definitive and intermediate hosts. After ingestion of cysts, the bradyzoites are released and infect the intestinal epithelial cells and are transformed into tachyzoites, which are disseminated in the host.

The strains of *T. gondii* are classified according to their degree of virulence in vivo: the type I strains (i.e. the strain RH) are highly virulent whereas the type II strains (i.e. the strains ME49, 76K or Pru) and type III strains (i.e. the strains CEP or M7741) are less virulent and generally establish chronic infections. Moreover, numerous atypical strains not assignable to the first three types have been identified, in particular in Africa and in South America (Howe D K et al., 1995, *J. Infect. Dis.*, 171, 1561-1566; Rajendran C et al., 2011, *Infect. Genet. Evol.*, 12, 359-368; Mercier A et al., 2010, *PLoS Negl. Trop. Dis.*, 4, e876).

Recently, an attenuated live strain of *Toxoplasma gondii*, the parasite responsible for toxoplasmosis, was developed by silencing two genes coding for the proteins TgMIC1 and TgMIC3 (EP 1 703 914 B1 and U.S. Pat. No. 7,964,185 B2/Cérède et al., 2005, *J. Exp. Med.*, 201: 453-63). This strain, designated Toxo mic1-3 KO, generated a strong and specific immune response against *Toxoplasma gondii* and makes it possible to prevent the effects of subsequent infection in the mouse (Ismaël et al., 2005, *J. Infect. Dis.*, 194: 1176-1183) and in the ewe (Mevelec et al., 2010, *Vet. Res.*, 41: 49). It has also been demonstrated that virulence in vivo is only very slightly affected by isolated inactivation of TgMIC1 or of TgMIC3; in contrast, it is greatly reduced by simultaneous inactivation of both proteins, demonstrating the synergistic role of the two proteins (Cérède et al., 2005 *J. Exp. Med.*, 201: 453-63).

*Neospora caninum* is an intracellular parasite, responsible for neosporosis. It also belongs to the Sarcocystidae family. The life cycle of *Neospora caninum* is very similar to that of *T. gondii* with two distinct phases: a sexual phase in the final host (i.e. the canids and the dog in particular) which leads to the production of oocysts, containing sporozoites, which are eliminated in the faeces, and an asexual phase in an intermediate host (i.e. ovines, caprins, bovines, equines, etc.), which leads to the production of tachyzoites and then cysts containing the bradyzoites.

More recently, an attenuated live strain of *Neospora caninum* was obtained, the strain Neo ncmic1-3 KO, in which the ncmic1 and ncmic3 genes were knocked out by homologous recombination. In this strain, the ncmic3 gene is replaced by a DHFR cassette, which confers resistance to pyrimethamine, and the ncmic1 gene is replaced by a CAT-GFP cassette, which endows the parasite with resistance to chloramphenicol and makes the parasite fluorescent. The parasite no longer expresses the NcMIC1 and NcMIC3 proteins. It has been shown that this mutant strain has infectious and immunogenic properties, endowing mammals with vaccine protection against the harmful effects of neosporosis.

*Toxoplasma gondii* and *Neospora caninum* have in common a specific process of invasion of the host cells in several steps leading to the formation of a parasitophorous vacuole in which the parasite multiplies and develops.

The Cryptosporidiidae constitute another family belonging to the phylum of the apicomplexans and are responsible for cryptosporidiosis, an extremely common disease which in particular affects humans and many animal species including farm animals (ovin, caprin, bovine, etc.) by the ingestion of parasites present in their food. The parasite then multiplies in the intestines, firstly asexually and then, secondly, sexually. The contaminated individuals excrete and disseminate new parasites, thus contaminating their environment (i.e. pastureland, water, etc.).

Several species of Cryptosporidiidae have been identified, among which *Cryptosporidium parvum* is one of the commonest and most virulent.

In humans, cryptosporidiosis is generally a benign disease. However, the consequences of this disease, the incidence of which is increasing every year, in particular in the United States, may be extremely serious in young children and immunodepressed persons, especially patients infected with the HIV virus. Thus, within these populations, cryptosporidiosis is responsible for severe diarrhoea that may cause significant dehydration or, without suitable treatment, even death of the individual.

In immunocompetent adult animals, cryptosporidiosis is also benign. Conversely, cryptosporidiosis generally has grave consequences in very young animals, a few days to a few weeks old, and whose immune system is immature. Thus, *Cryptosporidium* spp, and in particular *C. parvum*, has proved to be one of the commonest etiological agents of neonatal diarrhoea, which causes severe growth retardation and without suitable treatment may be fatal to the animal.

Neonatal diarrhoea constitutes a constant threat for breeders of bovines, ovines and caprins, and represents a considerable economic loss due to the loss of income resulting from retardation of growth, mortality of neonates, intervention of veterinarians and the costs of therapeutic treatment and rehydration. The etiology of neonatal diarrhoea is often multiple, several infectious agents in fact being responsible for these symptoms, in particular rotaviruses, coronaviruses, BVDV (Bovine Viral Diarrhoea Virus), *Escherichia coli* and, of course, *C. parvum*. The role of these various infectious agents in neonatal diarrhoea of ruminants is difficult to estimate as diagnostics is rarely carried out and there are regularly multiple infections. However, *C. parvum* is currently considered to be the main factor in neonatal diarrhoea (de Graaf et al., 1999, *Int. J. Parasitol.*, 29: 1269-1287). Thus, a study carried out on calves with neonatal diarrhoea demonstrated that 40% of them were infected with *C. parvum* and three-quarters of them did not have any other infectious agent (data from "Veterinary and Agrochemical Research Centre" in Brussels).

In order to reduce the intensity and duration of the symptoms, numerous molecules have been evaluated in various models, but none has given satisfactory results. Thus, in domestic ruminants, only halofuginone lactate (HaloCur®) and paromycin have produced useful results, but do not allow complete control of the parasite (Chartier, 2002, Le Point vétérinaire Pathologie ovine et caprine [The veterinary perspective. Pathologies of sheep and goats], 112-117). In humans, and especially for treating AIDS patients, the usual treatment is based on the use of paromomycin (Humatin) or nitazoxanide. The two molecules have similar efficacy but nitazoxanide is judged less toxic. Moreover, specific inhibitors of calcium-dependent protein kinases of *T. gondii* and of *C. parvum* have recently been developed (WO 2011/094628 A1). These are in particular compounds belonging to the classes of the pyrazolopyrimidines and the imidazo[1,5-α]pyrazines. These inhibitors affect the capacity of the parasites for invasion and proliferation, without disturbing the biological activities of the host cell.

In conclusion, whether in humans or animals, at present there is no specific treatment making it possible to effectively combat cryptosporidiosis, and only prevention, based on strict rules of hygiene, allow a reduction in the ingestion of water or foodstuffs contaminated with *C. parvum*.

There is consequently a real need for agents for the prevention and treatment of cryptosporidiosis in mammals, in particular mammals that have an immature or deficient immune system. In fact, as infection may occur during the first few days, the neonates have an immune system that is still developing, making a conventional vaccination scheme impossible in young mammals. Thus, prophylactic trials conducted with killed parasites on neonate calves in a region where the disease is highly endemic did not show any significant protection (Harp et al., 1996, *Am. J. Vet. Res.*, 57: 1586-1588; Harp et al., 1998, *J. Dairy. Sci.* 81: 289-294).

It has, however, been demonstrated that the immune response to *C. parvum* leads to the development of a protective response of type Th1 with considerable production of the cytokines IL-12 and IFN-γ. It has also been demonstrated that these cytokines are able to lessen the impact of infection (Lacroix et al., 2001, *Infect. Immun.*, 69: 1635-42).

One of the aims of the invention is to provide an immunostimulant capable of inducing a non-specific immune response in the neonate, with the production of IL-12 and IFNγ.

Another aim of the invention is to provide an immunostimulant capable of limiting the effects of infection of mammals, human or animal, by *Cryptosporidium parvum*.

Yet another aim of the invention is to provide a prophylactic treatment, and in particular a vaccine, against cryptosporidiosis.

The present invention relates to strains of Sarcocystidae selected from *Toxoplasma* spp or *Neospora* spp, isolated from their natural environment and having an immunostimulant effect, for the use thereof in the prevention or the treatment, in a mammal, of a disorder associated with an apicomplexan of the family Cryptosporidiidae.

The present invention relates to attenuated strains of Sarcocystidae selected from attenuated *Toxoplasma* spp or attenuated *Neospora* spp, isolated from their natural environment and having an immunostimulant effect, for the use thereof in the prevention or the treatment, in a mammal, of a pathology associated with an apicomplexan of the family Cryptosporidiidae.

The present invention relates to strains of Sarcocystidae selected from *Toxoplasma* spp or *Neospora* spp isolated from their natural environment and having an immunostimulant effect, for the use thereof in the prevention or the treatment, in a mammal, of a pathology associated with an apicomplexan of the family Cryptosporidiidae, said strains having attenuated virulence relative to the wild strains that induce a pathology associated with *Toxoplasma* spp or *Neospora* spp.

By way of example, without limiting the scope of the present invention, such wild strains of apicomplexans may be illustrated by a virulent strain of *T. gondii* of type RH for toxoplasmosis, or a virulent strain of *N. caninum* of type NC1 for neosporosis.

The present invention relates to strains of Sarcocystidae selected from *Toxoplasma* spp or *Neospora* spp isolated from their natural environment and having an immunostimulant effect, for the use thereof in the prevention or the treatment, in a mammal, of a pathology associated with an apicomplexan of the family Cryptosporidiidae, said strains having attenuated virulence relative to a virulent strain, i.e. a strain having virulence substantially identical to the virulence of the strain from which the strain with attenuated virulence was obtained.

By "immunostimulant" is meant the ability of a strain of *Toxoplasma* spp or *Neospora* spp to induce early activation of the immune system of the host. This activation involves components of the immune system such as interferons, cytokines, phagocytic cells, NK (Natural Killer) cells, dendritic cells and the complement system, which will act in a non-specific fashion on the targeted pathogen. This immunostimulation is not based on the establishment of adaptive immunity.

By "prevention" is meant prophylaxis with the aim of preventing the appearance or spreading of a disease. It is in particular a question of protecting an individual with predisposition to contracting and developing a disorder associated with an apicomplexan of the family Cryptosporidiidae. Such individuals are in particular neonates that have an immature immune system or individuals with an immune system dysfunction. It is also a question of protecting a mammal exposed to a risk of contamination from its environment.

By "treatment" is meant not only inhibition of the progression of the pathology but also attenuation of the symptoms associated with this pathology. The treatment has the aim of reducing the extent of the symptoms until they disappear completely, allowing the individual to recover a normal physiological state.

By "mammal" is meant human beings, certain commercial or farm animals and certain pet animals.

By "attenuated strains of *Toxoplasma* spp or *Neospora* spp" is meant strains of *Toxoplasma* spp or *Neospora* spp having an attenuated virulence, less than the virulence of the wild strains of *T. gondii* or of *N. caninum* capable of inducing a pathology, but which nevertheless conserve immunogenicity so as to be able to be used in the prevention or the treatment of a disorder associated with an apicomplexan of the family Cryptosporidiidae. The attenuation of virulence may result either from a natural process of evolution of the species or may be induced in particular by techniques of molecular biology familiar to a person skilled in the art. Whether it is of natural origin or the result of human activity, the attenuation of virulence is due to the absence of expression of virulence factors or to the expression of one or more virulence factors that are non-functional or have an altered function. The in vitro modification of the genetic heritage of *Toxoplasma* spp or *Neospora* spp confers a mutant character on the strain, relative to the wild-type strain from which it is derived. The wild strains of parasites not only have an immunogenic potential but are also virulent, i.e. they are capable of inducing a pathology associated with *Toxoplasma* spp or *Neospora* spp (i.e. toxoplasmosis and neosporosis respectively), making their use unsuitable in the context of the present invention. The virulence of the strains of *Toxoplasma* spp or of *Neospora* spp may in particular be evaluated by in vitro cellular infectivity tests or by infectivity tests in animals.

The cellular infectivity tests are carried out by depositing tachyzoites on confluent cells, for example HFF (Human Foreskin Fibroblast) cells or Vero cells, cell lines frequently used for the production of tachyzoites of *T. gondii* or of *N. caninum*. The number of vacuoles formed and the number of parasites in each vacuole is determined by microscopic observation. For the infectivity tests in animals, the various strains are injected into the animals and the survival of these animals is monitored over time (Cérède et al., 2005).

By "pathologies associated with an apicomplexan of the family Cryptosporidiidae" is meant the diseases resulting from an infection by a protozoon belonging to the phylum of the apicomplexans, and in particular parasites belonging to the family Cryptosporidiidae, which comprises the genus *Cryptosporidium*. Several tens of species of *Cryptosporidium* are referenced (Fayer R, 2010, *Exp. Parasitol.*, 124, 90-7). These parasites are capable of invading the mucosal epithelia.

According to a particular embodiment, in the use according to the present invention of the strains of Sarcocystidae selected from *Toxoplasma* spp or *Neospora* spp isolated from their natural environment and having an immunostimulant effect, said mammal is a neonate.

The present invention relates to strains of Sarcocystidae selected from *Toxoplasma* spp or *Neospora* spp, isolated from their natural environment and having an immunostimulant effect, for use in the prevention or the treatment, in a neonate mammal, of a pathology associated with an apicomplexan of the family Cryptosporidiidae.

By "neonate" is meant a mammal from the time of its birth until it is weaned, i.e. until the moment when the mammal becomes capable of feeding itself and is no longer dependent on its mother's milk. The main advantage of using the mutant strain of *Toxoplasma* spp or *Neospora* spp for the prevention and/or the treatment of pathologies associated with an apicomplexan of the family Cryptosporidiidae in the neonate is stimulation of its immature immune system in order to induce a non-specific immune response by synthesizing molecules that inhibit the growth of the Apicomplexa.

According to a particular embodiment, in the use according to the present invention of the strains of Sarcocystidae selected from *Toxoplasma* spp or *Neospora* spp isolated from their natural environment and having an immunostimulant effect, said mammal is a human being or an animal.

The animals to which the present invention relates are mainly commercial or farm animals, which are of interest to the agricultural and food industries, but also certain pet animals.

According to a more particular embodiment, in the use according to the present invention of the strains of Sarcocystidae selected from *Toxoplasma* spp or *Neospora* spp isolated from their natural environment and having an immunostimulant effect, said animal belongs to the group comprising or constituted by of ovines, caprids, porcines, bovines, equines, camelids, canids or felids (Fayer, 2004, *Vet. Parasitol.*, 126, 37-59).

According to another embodiment, in the use according to the present invention of the strains of Sarcocystidae selected from *Toxoplasma* spp or *Neospora* spp isolated from their natural environment and having an immunostimulant effect, said strains of *Toxoplasma* spp or of *Neospora* spp have at least an adhesin MIC1 and/or an adhesin MIC3 inactivated by a genetic modification relating to at least one of the genes mic1 and/or mic3.

By "an adhesin MIC1 and/or an adhesin MIC3" is meant the proteins of the micronemes, also called adhesins, MIC1 and/or MIC3 which play a role in the mobility, the migration or the invasion of parasites of the phylum Apicomplexa in its host. These proteins have linkage modules that allow them to bind to the target cells of the host.

By "an inactivated adhesin" is meant an adhesin the function of which can no longer be ensured within the cell. An adhesin is inactivated when it is not produced or when it is produced but does not have functional activity or has reduced functional activity. The inactivation also relates to an adhesin that can no longer bind to other proteins in order to form a complex.

By "genetic modification" is meant any mutation made in the nucleic acid sequence of a gene leading to the absence of expression of the protein encoded by that gene or leading to expression of a non-functional or less functional form of the protein encoded by that gene. This operation requires human intervention when it is carried out in vitro. This mutation may consist of the deletion of all or part of the gene, or of its coding region, or of its promoter region, and of the insertion or the substitution of nucleotides in the nucleotide sequence of the gene.

By "mic1 gene" is meant the gene coding for the protein of the micronemes MIC1, also called adhesin MIC1. This protein contains several modules, including binding domains that bind lactose specifically. The protein MIC1 is also capable of binding to the surface of the host cells.

The detailed construction of the Toxo mic1 KO strain is described in documents U.S. Pat. No. 7,946,185 B2 and EP 1 703 914 B1. The detailed construction of the Neo ncmic1 KO strain is described in the present application.

By "mic3 gene" is meant the gene coding for the protein of the micronemes MIC-3, also called adhesin MIC3. This protein homodimerizes in order to form a complex of 90 kDa. MIC3 comprises domains of the EGF type and a domain of the lectin type. The protein MIC3 is also capable of binding to the surface of the host cells.

The detailed construction of the Toxo mic3 KO strain is described in documents U.S. Pat. No. 7,946,185 B2 and EP 1 703 914 B1. The detailed construction of the Neo ncmic3 KO strain is described in the present application.

According to another particular embodiment, in the use according to the present invention of the strains of Sarcocystidae selected from *Toxoplasma* spp or *Neospora* spp isolated from their natural environment and having an immunostimulant effect, said strains of *Toxoplasma* spp or of *Neospora* spp have the two adhesins MIC1 and MIC3 inactivated by a genetic modification relating to the two genes mic1 and mic3.

By "genetic modification relating to the two genes mic1 and mic3" is meant the mutation made in the nucleic acid sequence of the mic1 gene and in that of the mic3 gene. This double mutation leads to the absence of expression of the proteins MIC1 and MIC3 or leads to the expression of a non-functional or less functional form of the proteins MIC1 and MIC3. These mutant strains of *Toxoplasma* spp or of *Neospora* spp are called Toxo mic1-3 KO or Neo ncmic1-3 KO respectively and have a very attenuated virulence in comparison with the wild strains of *T. gondii* of type RH or of *N. caninum* of type NC1 from which they are derived. However, the Toxo mic1-3 KO or Neo ncmic1-3 KO strains retain a strong immunogenicity. The detailed construction of the Toxo mic1-3 KO strain is described in documents U.S. Pat. No. 7,946,185 B2 and EP 1 703 914 B1. The detailed construction of the Neo ncmic1-3 KO strain is described in the present application.

The Toxo mic1-3 KO and Neo ncmic1-3 KO strains retained their capacity for colonizing the target tissues without the development of a pathogenic effect following administration of said strains to a mammal. The knock out of the genes mic1 and mic3 has little or no effect on the immunogenic potential of these strains, but reduces their virulence considerably relative to a virulent strain, i.e. a strain having a virulence substantially identical to the virulence of the strain from which the strain with attenuated virulence was obtained.

The inoculation of the Toxo mic1-3 KO strain in neonate mice leads to the production of cytokines IL-12 and IFN-γ and effectively protects the mouse pups from subsequent infection with *Cryptosporidium parvum*.

The mutant Toxo mic1-3 KO strain effectively stimulates the production of IL-12 and IFN-γ from cells of the mesenteric lymph nodes and splenocytes of lambs, confirming the possibility of using this mutant strain as an immunostimulant in this target animal species.

According to a particular embodiment, in the use according to the present invention of the strains of Sarcocystidae selected from *Toxoplasma* spp or *Neospora* spp isolated from their natural environment and having an immunostimulant effect, said strains of *Toxoplasma* spp or of *Neospora* spp are respectively *Toxoplasma gondii* or *Neospora caninum*.

According to another embodiment, in the use according to the present invention of the strains of Sarcocystidae selected from *Toxoplasma* spp or *Neospora* spp isolated from their natural environment and having an immunostimulant effect, said immunostimulant effect of said strains leads to the secretion of interleukin-12 (IL-12) and then of interferon-γ (IFN-γ).

By "interleukin-12 (IL-12)" is meant the cytokine synthesized by immune system cells such as the monocytes, the dendritic cells and the macrophages. The cytokine is secreted early and will thus activate the target cells (T cells and Natural Killer cells) so that the latter secrete IFN-γ in their turn.

By "interferon-γ (IFN-γ)" is meant the cytokine synthesized by the T lymphocytes CD4+, CD8+ and the Natural Killer (NK) cells activated by IL-12. The secretion of IFN-γ by the cells of the organism will allow production of an innate response protective against *C. parvum*. This cytokine will have a pleiotropic activity owing to the diversity of the targeted cell lines.

By "cytokines" is meant all the molecules involved in the development and the regulation of the immune system. The cytokines are glycosylated or non-glycosylated proteins, which may be classified according to their biological activity:
  pro-inflammatory: this includes the interleukins (IL) and the tumour necrosis factors (TNF),
  immunoregulatory: this includes the interleukins (IL),
  effector: this includes the interferons (IFN), the tumour necrosis factors (TNF) and the chemokines.

According to another more particular embodiment, in the use according to the present invention of the strains of Sarcocystidae selected from *Toxoplasma* spp or *Neospora* spp isolated from their natural environment and having an immunostimulant effect, said secretion of interleukin-12 (IL-12) and of interferon-γ (IFN-γ) begins between 3 and 9 days after using said strains of *Toxoplasma* spp or of *Neospora* spp as immunostimulant.

According to a more particular embodiment, in the use according to the present invention of the strains of Sarcocystidae selected from *Toxoplasma* spp or *Neospora* spp isolated from their natural environment and having an immunostimulant effect, said pathology associated with an apicomplexan of the family Cryptosporidiidae is cryptosporidiosis.

By "cryptosporidiosis" is meant the pathology characterized by symptoms such as cramps, fever, fatigue, nausea and especially diarrhoea, which may lead to the dehydration of the mammal infected by *Cryptosporidium parvum* or by another *Cryptosporidium* species. Cryptosporidiosis mainly affects the intestines of mammals but may also infect the biliary and pancreatic tracts and the respiratory tract in an immunodepressed individual. The infestation occurs by ingestion of oocysts present in the excrement of parasitized animals with which the environment is contaminated (water, earth or raw food). The symptoms appear two to ten days after the infection occurred and persist for more than two weeks. The severity of this pathology varies depending on the age of the infected host but more particularly on the state of its immune system. In a host having a mature and functional immune system, cryptosporidiosis has no effect on the health of the host. Conversely, a host that is very young, very old or has an immature or deficient immune system may develop very severe forms of cryptosporidiosis.

By "immature or deficient immune system" is meant the immune system for which one or more cell lines are either absent, or deficient. The immaturity of the immune system is a common trait in neonate mammals, which makes them particularly vulnerable to parasitic infections. The absorption of antibodies from the mother via the colostrum endows the neonate with a certain degree of protection while its immune system is being established. The immaturity or the deficiency of the immune system may also result from pathologies of a genetic origin, in particular in humans, such as Wiskott-Aldrich syndrome, an X-linked lymphoproliferative syndrome. This deficiency may also arise after an infection by the human immunodeficiency virus (HIV) or following a therapeutic treatment associated with an organ graft or the medical management of certain cancers by chemo- or radiotherapy. The mammals that have an immature or deficient immune system are particularly vulnerable to infections with apicomplexans.

According to an even more particular embodiment, in the use according to the present invention of the strains of Sarcocystidae selected from *Toxoplasma* spp or *Neospora* spp isolated from their natural environment and having an immunostimulant effect, said apicomplexan of the family Cryptosporidiidae responsible for cryptosporidiosis is at least one apicomplexan selected from the group constituted by *Cryptosporidium parvum, Cryptosporidium bovis, Cryptosporidium andersoni, Cryptosporidium ryanae, Cryptosporidium muris, Cryptosporidium ubiquitum, Cryptosporidium hominis, Cryptosporidium canis, Cryptosporidium felis, Cryptosporidium baileyi, Cryptosporidium meleagridis* or *Cryptosporidium xiaoi*.

By "*Cryptosporidium parvum, Cryptosporidium bovis, Cryptosporidium andersoni, Cryptosporidium ryanae, Cryptosporidium muris, Cryptosporidium ubiquitum, Cryptosporidium hominis, Cryptosporidium canis, Cryptosporidium felis, Cryptosporidium baileyi, Cryptosporidium meleagridis* or *Cryptosporidium xiaoi*" is meant the protozoa of the phylum Apicomplexa capable of causing intestinal pathologies of a hydric nature in the majority of mammals. These parasites are in particular capable of causing cryptosporidiosis in ovines, caprins, porcines, bovines, equines, camels, camelids, canids, felids or humans (Fayer, 2004, *Vet. Parasitol.*, 126, 37-59) that have an immature or deficient immune system.

The present invention also relates to the strains of *Toxoplasma gondii* or of *Neospora caninum* that have the two adhesins MIC1 and MIC3 inactivated by a genetic modification relating to the two mic1 and mica genes for the use thereof in the prevention or the treatment, in a mammal, of a pathology associated with an apicomplexan of the family Cryptosporidiidae, said pathology associated with an apicomplexan of the family Cryptosporidiidae being cryptosporidiosis.

The present invention also relates to the strains of *Toxoplasma gondii* or of *Neospora caninum* isolated from their natural environment and having an immunostimulant effect, for use in the prevention or the treatment, in a mammal, of a pathology associated with an apicomplexan of the family Cryptosporidiidae, said strains of *Toxoplasma gondii* or of *Neospora caninum* having the two adhesins MIC-1 and MIC-3 inactivated by a genetic modification relating to the two mic-1 and mic-3 genes, and said pathology associated with an apicomplexan of the family Cryptosporidiidae is cryptosporidiosis.

The invention also relates to the strains of *Toxoplasma gondii* or of *Neospora caninum* isolated from their natural environment and having an immunostimulant effect, said strains of *Toxoplasma gondii* or of *Neospora caninum* having the two adhesins MIC1 and MIC3 inactivated by a genetic modification relating to the two mic1 and mic3 genes for the use thereof in the prevention or the treatment, in a mammal, of a pathology associated with an apicomplexan of the family Cryptosporidiidae, said strains of *Toxoplasma gondii* or of *Neospora caninum* being administered to said mammal at a rate from 20 to $10^9$ tachyzoites.

By "tachyzoite" is meant the rapidly multiplying form of *Toxoplasma gondii* or of *Neospora caninum*. The tachyzoite has a crescent shape and a variable size of 5-8×2-3 μm. The apical part of the parasite comprises conoids which participate in the penetration of the parasite into the host cell. The micronemes, the rhoptries and the dense granules constitute the three major organelles of the tachyzoite, which also comprises a nucleus, an apicoplast, a Golgi apparatus, an endoplasmic reticulum and an organite similar to the mitochondrion.

The determination of an effective dose of tachyzoites for the prophylactic treatment of mammals makes it possible to limit the infection or the transmission of the pathogenic agent responsible for cryptosporidiosis. Such a treatment may be adapted and/or repeated as many times as necessary by a person skilled in the art, depending on the age and immunological status of the mammal.

The tachyzoites may be brought into contact with the mammal not only on a mammal presenting the symptoms characteristic of cryptosporidiosis but also on a mammal without any of the symptoms of cryptosporidiosis but which is in contact with other mammals infected by *Cryptosporidium parvum* or by another species of *Cryptosporidium* able to induce cryptosporidiosis.

According to a particular embodiment, the strains of Sarcocystidae selected from *Toxoplasma* spp or *Neospora* spp isolated from their natural environment and having an immunostimulant effect for the use thereof according to the present invention are in a galenic form selected from the group comprising or constituted by liquid suspensions, solid or liquid dispersions, powders, pastes or lyophilizates.

The galenic form is adapted by a person skilled in the art depending on the method of administration selected. All the conventional methods of administration may be envisaged: by parenteral route (intravenous, subcutaneous, intradermal, intramuscular, intraperitoneal, and intranasal) or by enteral route.

According to a more particular embodiment, the strains of Sarcocystidae selected from *Toxoplasma* spp or *Neospora* spp isolated from their natural environment and having an immunostimulant effect for the use thereof according to the present invention are associated with at least one other antigen, or at least one adjuvant, or at least one stabilizer, or at least one preservative or a mixture of at least two of said products for increasing the immune response of said mammal.

By "antigen" is meant any natural or recombinant protein, in its native or mutated form, originating from a parasite or from a pathogen other than *Toxoplasma* spp or *Neospora* spp capable of inducing a cellular or humoral immune response in a mammal. The aim of combining the mutant strain of *Toxoplasma* spp or *Neospora* spp with such an antigen is to amplify the mammal's immune response and thus endow it with better protection against an apicomplexan infection.

By "adjuvant" is meant any substance capable of reinforcing and prolonging the immune response directed against the targeted antigen. The mechanism involved in order to make the immune response more effective is dependent on the adjuvant used. The adjuvants are substances which are well known to a person skilled in the art and in particular include aluminium salts, squalene, saponins, the bacterial constituents or toxins, or also certain proteins (peptone, albumin, casein).

By "stabilizers or preservatives" is meant the compounds allowing perfect preservation of the strains of *Toxoplasma* spp or *Neospora* spp in their packaging.

Stabilizers or preservatives are substances which are well known to a person skilled in the art and in particular include the carbohydrates (sorbitol, mannitol, lactose, sucrose, glucose, dextran, trehalose), the polar organic solvents, such as DMSO (dimethylsulphoxide), and the polysorbates.

By "to increase the immune response" is meant the activation of various pathways of the immune system. In a mammal that has an immature or deficient immune system, it is a question of activating the non-specific response by increasing the synthesis of different categories of cytokines, such as the interferons or the interleukins. Among these cytokines interleukin-12 (IL-12) may be mentioned, which will activate the CD4+ or CD8+ LT cells as well as the NK cells. These activated cells will in their turn secrete interferon γ (IFN-γ), which plays a role in the immunological mechanisms that control the multiplication of many intracellular parasites, thus preventing their propagation in the organism. In an adult mammal having a mature immune system, the increase in the immune response passes via an adaptive immunity (specific proliferation in response to the foreign antigens) in addition to the non-specific response.

The present invention also relates to a method of inducing an immune response in a mammal comprising a step of administration, to said mammal, of tachyzoites of strains of Sarcocystidae selected from *Toxoplasma* spp or *Neospora* spp, isolated from their natural environment and having an immunostimulant effect, allowing an immune response to be induced.

The present invention also relates to a method of inducing an immune response in a neonate mammal comprising a step of administration, to said neonate mammal, of tachyzoites of strains of Sarcocystidae selected from *Toxoplasma* spp or *Neospora* spp, isolated from their natural environment and having an immunostimulant effect, allowing an immune response to be induced.

By "immune response" is meant the two essential phases constituted by the recognition of the antigen and the reaction intended to eliminate said antigen. When an antigen enters the body for the first time, it is the non-specific immune response that is activated. It uses non-clonal mechanisms, since it does not require specific cellular clones. The inflammatory reaction created by this non-specific response will lead to adaptive immunity. This response involves cells specifically recognizing the antigen and will then lead to clonal expansion. This clonal expansion will result in a very effective immune response and a memory response (specific immune response following the second entry of the antigen into the organism).

According to a particular embodiment, in the method according to the present invention, said mammal is a neonate.

According to a more particular embodiment, in the method according to the present invention, said mammal is a human being or an animal.

According to an even more particular embodiment, in the method according to the present invention, the animal belongs to the group comprising or constituted by ovines, caprins, porcines, bovines, equines, camelids, canids or felids.

According to another embodiment, in the method according to the present invention, said strains of Sarcocystidae selected from *Toxoplasma* spp or *Neospora* spp have at least one adhesin MIC1 and/or one adhesin MIC3 inactivated by a genetic modification which relates to at least one of the mid and/or mic3 genes.

According to another particular embodiment, in the method according to the present invention, said strains of Sarcocystidae selected from *Toxoplasma* spp or *Neospora* spp have the two adhesins MIC1 and MIC3 inactivated by a genetic modification which relates to the two mic1 and mic3 genes.

According to another more particular embodiment, in the method according to the present invention, said strains of Sarcocystidae selected from *Toxoplasma* spp or *Neospora* spp are respectively *Toxoplasma gondii* or *Neospora caninum*.

According to yet another particular embodiment, in the method according to the present invention, the strains of Sarcocystidae selected from *Toxoplasma* spp or *Neospora* spp induce a non-specific immune response in particular characterized by the secretion of IL-12 and/or IFN-γ.

The present invention also relates to a method for protecting a mammal against a parasitosis associated with an apicomplexan of the family Cryptosporidiidae comprising a step of administration, to said mammal, tachyzoites of strains of Sarcocystidae selected from *Toxoplasma* spp or *Neospora* spp, isolated from their natural environment and having an immunostimulant effect, for inducing protection against said parasitosis.

According to a more particular embodiment, in the method according to the present invention, the mammal is a neonate.

According to an even more particular embodiment, in the method according to the present invention, the mammal is a human being or an animal.

According to a particular embodiment, in the method according to the present invention, the animal belongs to the group comprising or constituted by ovines, caprins, porcines, bovines, equines, camelids, canids or felids.

According to a particular embodiment, in the method according to the present invention, said strains of Sarcocystidae selected from *Toxoplasma* spp or *Neospora* spp have at least one adhesin MIC1 and/or one adhesin MIC3 inactivated by a genetic modification which relates to at least one of the mid and/or mic3 genes.

According to a more particular embodiment, in the method according to the present invention, said strains of Sarcocystidae selected from *Toxoplasma* spp or *Neospora* spp have the two adhesins MIC1 and MIC3 inactivated by a genetic modification which relates to the two mic1 and mic3 genes.

According to a more particular embodiment, in the method according to the present invention, said parasitosis associated with an apicomplexan of the family Cryptosporidiidae is cryptosporidiosis.

According to another more particular embodiment, in the method according to the present invention, the apicomplexan of the family Cryptosporidiidae responsible for the cryptosporidiosis is at least one apicomplexan selected from the group constituted by *Cryptosporidium parvum, Cryptosporidium bovis, Cryptosporidium andersoni, Cryptosporidium ryanae, Cryptosporidium muris, Cryptosporidium ubiquitum, Cryptosporidium hominis, Cryptosporidium canis, Cryptosporidium felis, Cryptosporidium baileyi, Cryptosporidium meleagridis* or *Cryptosporidium xiaoi.*

According to an even more particular embodiment, in the method according to the present invention, the administration, to said mammal, of said tachyzoites of said strains of Sarcocystidae selected from *Toxoplasma* spp or *Neospora* spp is carried out by enteral route or by parenteral route.

According to yet another embodiment, in the method according to the present invention, the administration, to said mammal, of said tachyzoites of said strains of Sarcocystidae selected from *Toxoplasma* spp or *Neospora* spp is carried out before exposure of said mammal to the apicomplexan of the family Cryptosporidiidae responsible for cryptosporidiosis.

According to yet another embodiment, in the method according to the present invention, the administration, to said mammal, of said tachyzoites of said strains of Sarcocystidae selected from *Toxoplasma* spp or *Neospora* spp is carried out during exposure of said mammal to the apicomplexan of the family Cryptosporidiidae responsible for cryptosporidiosis.

According to yet another embodiment, in the method according to the present invention, the administration, to said mammal, of said tachyzoites of said strains of Sarcocystidae selected from *Toxoplasma* spp or *Neospora* spp is carried out after exposure of said mammal to the apicomplexan of the family Cryptosporidiidae responsible for cryptosporidiosis.

In the aforementioned three embodiments, said mammal may be a neonate.

The following figures and examples are given purely by way of illustration of the subject of the present invention and do not in any way constitute a limitation thereof.

DESCRIPTION OF THE FIGURES

FIG. 2-A: this figure is a schematic representation of the pNcMic3KO-DHFR plasmid. This plasmid with 11,312 base pairs comprises the DHFR selection gene flanked by the homologous regions (5HR-NcMic3 and 3HR-NcMic3) of the sequences flanking the ncmic3 gene, the ampicillin resistance gene (Amp) as well as the Not I restriction site which permits its linearization.

FIG. 2-B: this figure is a schematic representation of the pNcMic1KO-CAT-GFP plasmid. This plasmid with 10,069 base pairs comprises the CAT-GFP selection gene flanked by the homologous regions (3HR-NcMic1 and 5HR-NcMic1) of the sequences flanking the ncmic1 gene, the ampicillin resistance gene (Amp) as well as the Kpn I restriction site which permits its linearization.

FIG. 3-A: this figure shows the electrophoretic profiles of the PCR products obtained respectively in the wild-type strain NC1 of *N. caninum* and in the mutant strain Neo ncmic3 KO, using the sets of PCR primers No. 1, No. 2 or No. 3 in Table II which correspond to SEQ ID NO: 5 to SEQ ID NO: 10.

FIG. 3-B: this figure shows the electrophoretic profiles of the PCR products obtained respectively in the wild-type strain NC1 of *N. caninum* and in the mutant strain Neo ncmic3 KO, using the sets of PCR primers No. 4, No. 5, No. 6 or No. 7 in Table II which correspond to SEQ ID NO: 11 to SEQ ID NO: 16.

FIG. 4-A: this figure illustrates the analysis for detecting the NcMIC3 protein in the wild-type strain NC1 of *N. caninum* by immunofluorescence, using an antibody specifically recognizing the NcMIC3 protein. One and the same microscopic field is visualized in direct light (image A) or in fluorescence (image B).

FIG. 4-B: this figure illustrates the analysis for detecting the NcMIC3 protein in the mutant strain of *N. caninum* Neo ncmic3 KO by immunofluorescence, using an antibody specifically directed against the NcMIC3 protein. One and the same microscopic field is visualized in direct light (image A) or in fluorescence (image B).

on the x-axis: batches of C57BL/6 mouse pups controls (A) and inoculated with the strain Toxo mic1-3 KO (B)
    on the y-axis: absorbance values measured at 405 nm.

Figure 7:
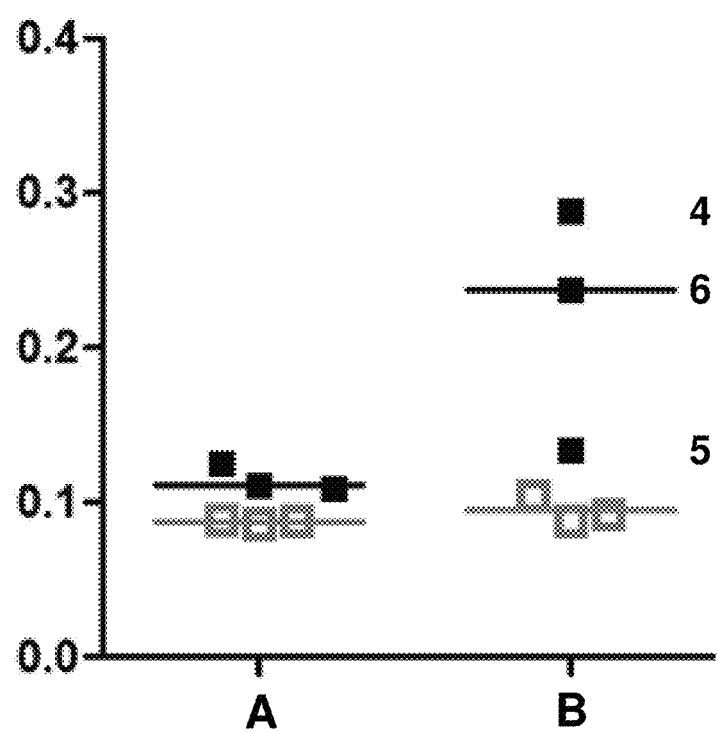
FIG. 7: illustrates the assay of antibodies of type IgM anti-*Toxoplasma gondii* in mouse pup serum. The assay of antibodies of type IgM anti-*Toxoplasma gondii* in the serum was carried out 3 days (empty grey squares) or 9 days (filled black squares) after the mouse pups had received 20 tachyzoites of the strain Toxo mic1-3 KO by intraperitoneal route. The mouse pups that had not received any tachyzoite of the strain Toxo mic1-3 KO served as controls.

The three mouse pups that received 20 tachyzoites of the strain Toxo mic1-3 KO and were sacrificed at 9 days are shown by their number (4, 5, 6) in FIG. 7.

FIG. 8-A: illustrates the measurement of the expression of interferon-gamma (IFN-γ) in the ileum of the mouse pup. The expression level of the gene coding for IFN-γ was measured by quantitative PCR on the total RNAs extracted from a fragment of ileum using specific primers (SEQ ID NO: 33 to 34), 9 days after the mouse pups had received 20 tachyzoites of the strain Toxo mic1-3 KO by intraperitoneal route (filled black squares). The mouse pups that had not received any tachyzoites of the strain Toxo mic1-3 KO served as controls (empty grey squares).

on the x-axis: batches of C57BL/6 mouse pups controls (A) and inoculated with the strain Toxo mic1-3 KO (B)
    on the y-axis: IFN-γ/HPRT ratio.

The three mouse pups that received 20 tachyzoites of the Toxo mic1-3 KO strain and were sacrificed at 9 days are shown by their number (4, 5, 6) in FIG. 8-A.

FIG. 8-B: illustrates the measurement of the expression of interleukin-12 (p40 subunit) (IL-12p40) in the mouse pup ileum. The expression level of the gene coding for IL-12p40 was measured by quantitative PCR on the total RNAs extracted from a fragment of ileum using specific primers (SEQ ID NO: 31 to 32), 9 days after the mouse pups received 20 tachyzoites of the strain Toxo mic1-3 KO by intraperitoneal route (filled black squares). The mouse pups that had not received any tachyzoites of the strain Toxo mic1-3 KO served as controls (empty grey squares):

on the x-axis: batches of C57BL/6 mouse pups controls (A) and immunostimulated by the strain Toxo mic1-3 KO (B)
    on the y-axis: IL-12p40/HPRT ratio.

The three mouse pups that received 20 tachyzoites of the strain Toxo mic1-3 KO and were sacrificed at 9 days are shown by their number (4, 5, 6) in FIG. 8-B.

Figure 9:
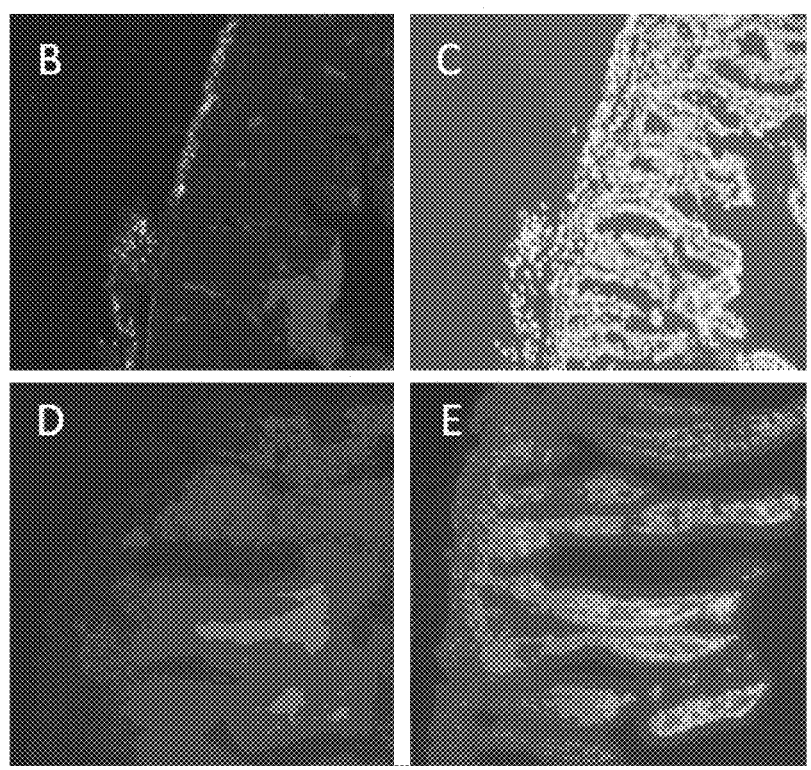

FIG. 9: illustrates the detection of the presence of tachyzoites of Toxo mic1-3 KO in the intestine of the mouse pup. The detection of the presence of tachyzoites of Toxo mic1-3 KO was carried out by immunohistology on sections of the intestine 9 days after the mouse pups received 20 tachyzoites of the strain Toxo mic1-3 KO by intraperitoneal route Immunolabelling is carried out using a rabbit anti-SAG-1 polyclonal antibody and an anti-rabbit secondary antibody coupled to fluorescein isothiocyanate.

The detection of tachyzoites of *Toxoplasma gondii* mic1-3 KO is shown for the intestines of the mouse pups No. 4 (B) and No. 6 (D). The tachyzoites appear in the form of white dots in the intestinal muscles of the mouse pup No. 4 (B). The nuclei of the cells of the intestinal villi and intestinal muscles of the mouse pups No. 4 (C) and No. 6 (E) are labelled with Hoechst and appear in the form of white dots.

Figure 10:
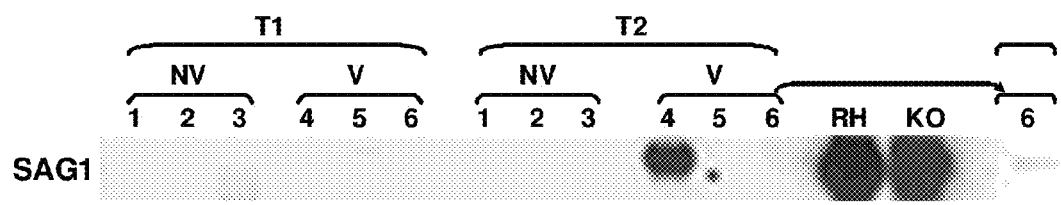

FIG. 10: illustrates the presence of *Toxoplasma gondii* via the expression of the surface antigen SAG-1 in the ileum of the mouse pup.

The cDNAs obtained from the total RNAs extracted from a fragment of ileum served as a matrix for the amplification of SAG-1 by PCR using specific primers (SEQ ID NO: 37 to 38). The mouse pups were sacrificed three days (T1) or 9 days (T2) after receiving 20 tachyzoites of the strain Toxo mic1-3 KO by intraperitoneal route (V). The mouse pups that had not received any tachyzoite of the strain Toxo mic1-3 KO served as controls (NV). The PCR products were deposited on agarose gel.

SAG-1 was also amplified from the genomic DNA of the wild-type strain of *Toxoplasma gondii* (RH) and from the genomic DNA of the mutated strain of Toxo mic1-3 KO (KO). The amplification products serve as controls of the size of the amplification product of SAG-1.

The mouse pups are shown by their number (1, 2, 3, 4, 5, 6) in FIG. 10.

Figure 11:
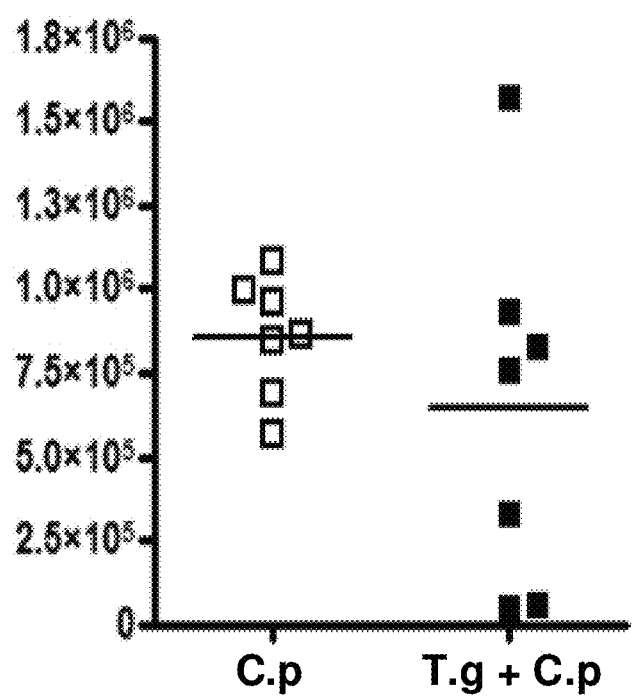

FIG. 11: illustrates the count of the oocysts of *Cryptosporidium parvum* in the intestine of the mouse pup. The number of oocysts of *Cryptosporidium parvum* was counted in a Thoma cell from an extract of ground material of the intestine placed in a sugar solution. The intestines originate from:
- the mouse pups challenged with 500 000 parasites of *Cryptosporidium parvum*, which had received 20 tachyzoites of the strain Toxo mic1-3 KO by intraperitoneal route 3 days prior the challenge with *Cryptosporidium parvum* (filled black squares), or
- the mouse pups challenged with 500 000 parasites of *Cryptosporidium parvum*, which had not received any tachyzoite of the strain Toxo mic1-3 KO (empty grey squares).

The mouse pups are sacrificed 6 days after the infection by *Cryptosporidium parvum*.
- on the x-axis: the batches of C57BL/6 mouse pups infected by *Cryptosporidium parvum* alone (C.p) or by Toxo mic1-3 KO and then *Cryptosporidium parvum* (T.g+C.p)
- on the y-axis: the total number of oocysts of *Cryptosporidium parvum* in the intestine.

Figure 12:
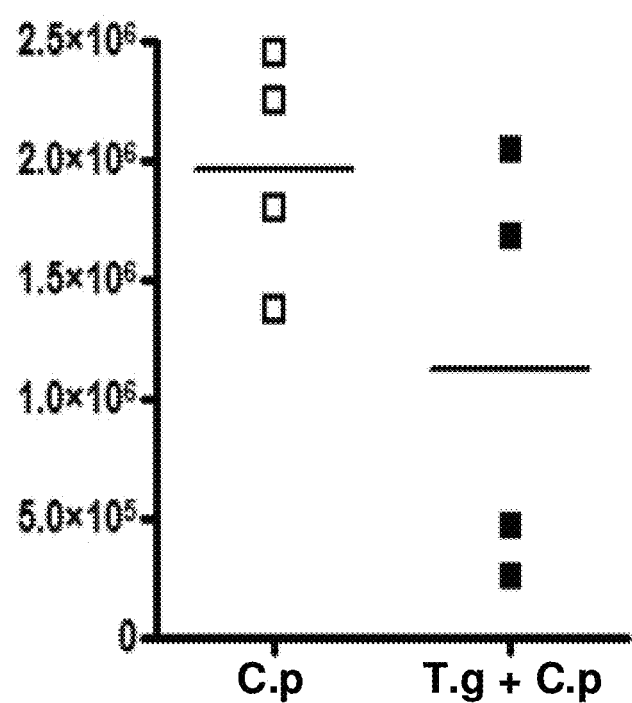

FIG. 12: illustrates the detection of the presence of oocysts of *Cryptosporidium parvum* in the intestine of the mouse pup. The number of oocysts of *Cryptosporidium parvum* was counted in a Thoma cell from an extract of ground material of the intestine placed in a sugar solution. The intestines originate from:
- the mouse pups challenged with 1 000 000 parasites of *Cryptosporidium parvum*, which had received 20 000 tachyzoites of the strain Toxo mic1-3 KO by oral route 3 days prior the challenge with *Cryptosporidium parvum* (filled black squares), or
- the mouse pups challenged with 1 000 000 parasites of *Cryptosporidium parvum*, which had not received any tachyzoite of the strain Toxo mid1-3 KO (empty grey squares).

The mouse pups are sacrificed 7 days after the infection by *Cryptosporidium parvum*.
- on the x-axis: the batches of C57BL/6 mouse pups infected by *Cryptosporidium parvum* alone (C.p) or by Toxo mic1-3 KO and then *Cryptosporidium parvum* (T.g+C.p)
- on the y-axis: the total number of oocysts of *Cryptosporidium parvum* in the intestine.

FIG. 13-A: illustrates the assay of interleukin-12 (IL-12) in the mononuclear cells from the spleen of lambs and of adult sheep. Samples of mononuclear cells from the spleen of lambs (grey triangles) and of adult sheep (black squares) were infected in vitro by three different strains of *Toxoplasma gondii*: type I wild-type strain (RH), type I mutant strain Toxo mic1-3 KO (KO) and type II wild-type strain (Pru). Mononuclear cells from the spleen of lambs and of adult sheep not infected in vitro serve as controls (M).
- on the x-axis: the "RH": type I wild-type strain of *Toxoplasma gondii*, "KO": strain Toxo mid 1-3 KO, "Pru" type II wild-type strain, "M": spleen cells cultured in vitro without stimulant (negative control)
- on the y-axis: the concentration of IL-12 (IU/ml).

FIG. 13-B: illustrates the assay of interleukin-12 (IL-12) in the mononuclear cells originating from the mesenteric lymph nodes of lambs and of adult sheep. Samples of mononuclear cells originating from the mesenteric lymph nodes of lambs (grey triangles) and of adult sheep (black squares) were infected in vitro by three different strains of *Toxoplasma gondii*: type I wild-type strain (RH), type I mutant strain Toxo mic1-3 KO (KO) and type II wild-type strain (Pru). Mononuclear cells from the mesenteric lymph nodes of lambs and of adult sheep not infected in vitro serve as controls (M).
- on the x-axis: the "RH": type I wild-type strain of *Toxoplasma gondii*, "KO": strain Toxo mic 1-3 KO, "Pru" type II wild-type strain, "M": spleen cells cultured in vitro without stimulant (negative control)
- on the y-axis: the concentration of IL-12 (IU/ml).

FIG. 13-C: illustrates the assay of interferon gamma (IFNγ) in the mononuclear cells from the spleen of lambs and of adult sheep. Samples of mononuclear cells from the spleen of lambs (grey triangles) and of adult sheep (black squares) were infected in vitro by three different strains of *Toxoplasma gondii*: type I wild-type strain (RH), type I mutant strain Toxo mic1-3 KO (KO) and type II wild-type strain (Pru). Mononuclear cells from the spleen of lambs and of adult sheep not infected in vitro serve as controls (M).
- on the x-axis: the "RH": type I wild-type strain of *Toxoplasma gondii*, "KO": strain Toxo mic 1-3 KO, "Pru" type II wild-type strain, "M": spleen cells cultured in vitro without stimulant (negative control)
- on the y-axis: the concentration of IFNγ (ng/ml).

Figure 14:
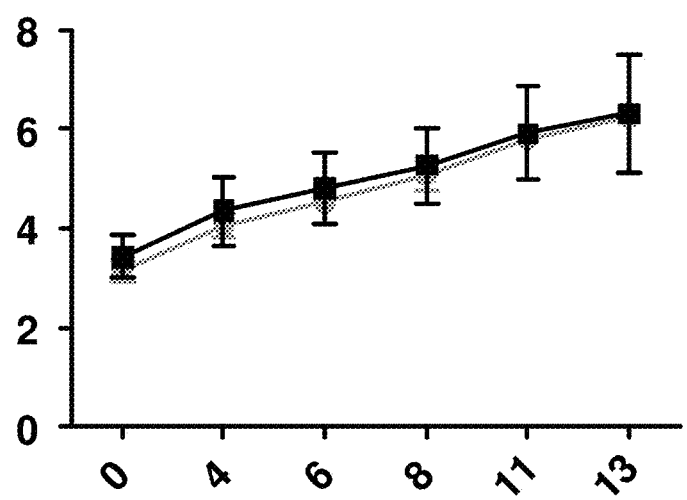

FIG. 14: illustrates the change in body weight of the lambs immunostimulated with $10^6$ tachyzoites Toxo mic1-3 KO, one day after their birth (batch A—black square) in comparison with control lambs not immunostimulated (batch B—grey circle).
- on the x-axis: the time elapsed after stimulation of the lambs by Toxo mic1-3 KO (in days)
- on the y-axis: the body weight of the lambs (in kilograms).

Figure 15:
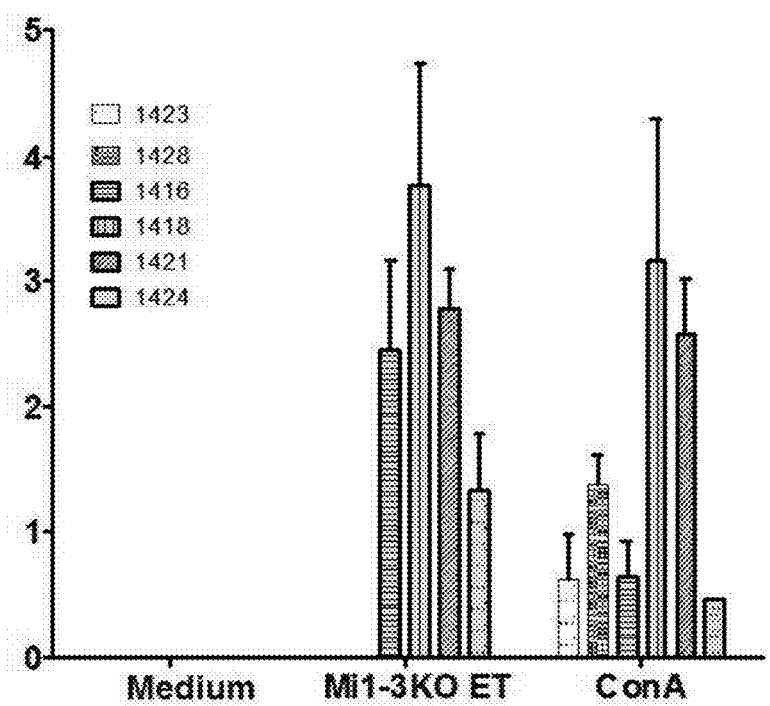

FIG. 15: illustrates the production of IFN-γ after restimulation with the total extract of the strain Toxo mic1-3 KO of mononuclear cells of the spleen of lambs immunostimulated with $10^6$ tachyzoites Toxo mic1-3 KO, one day after their birth (lambs No. 1416-1418-1421 and 1424) or of control lambs (lambs 1428 and 1423), sacrificed 15 days after the immuno stimulation, on the x-axis: the "medium": spleen cells cultured in vitro without stimulant (control −), "Mic1-3 KO ET: spleen cells restimulated with the total parasite extract of the strain Toxo mic1-3 KO and "ConA": spleen cells stimulated by concanavalin A (control+)]

on the y-axis: the concentration of IFN-γ (in ng/ml).

Figure 16:
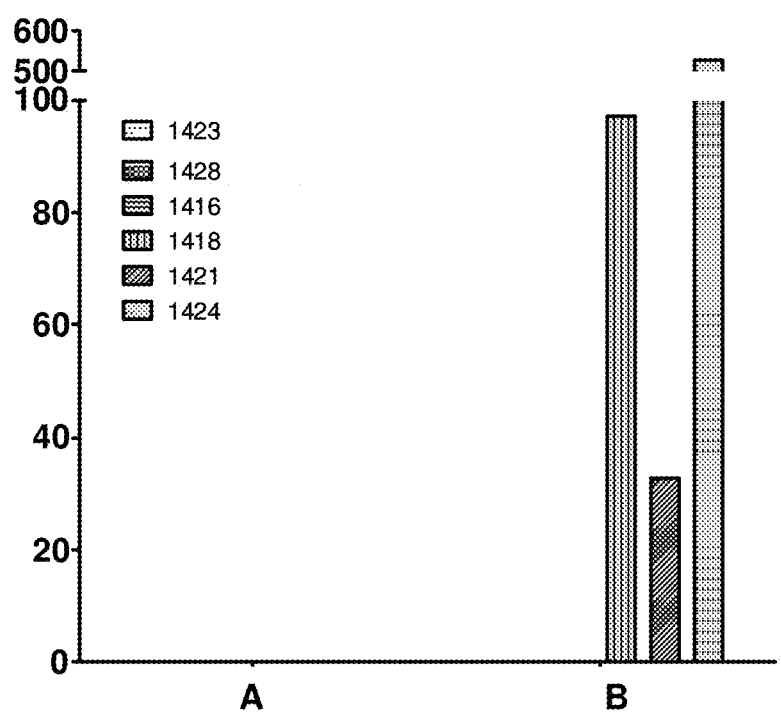

FIG. 16: illustrates the production of IFN-γ produced from the ex vivo culture of cells of subiliac and popliteal lymph nodes of lambs immunostimulated with $10^6$ tachyzoites Toxo mic1-3 KO, one day after their birth (lambs No. 1416-1418-1421 and 1424) or of control lambs (lambs 1428 and 1423), sacrificed 15 days after the immunostimulation.

on the x-axis: the cells of popliteal lymph nodes (A) and cells of subiliac lymph nodes (B)

on the y-axis: the concentration of IFN-γ (in pg/ml).

Figure 17:
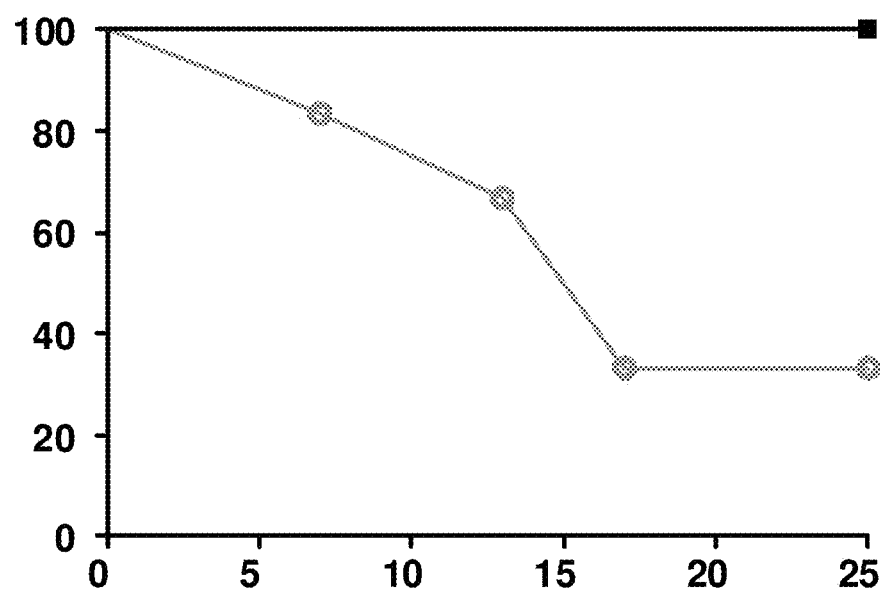

FIG. 17: illustrates the survival of lambs immunostimulated with $10^6$ tachyzoites Toxo mic1-3 KO, one day after their birth and challenged with $5.10^6$ oocysts of *C. parvum* (black square) and the control lambs only challenged (grey circle). The survival curves are of the Kaplan-Meier type.

on the x-axis: the time elapsed after infection of the lambs by *C. parvum* (in days)

on the y-axis: the survival of the lambs (in %).

Figure 18:
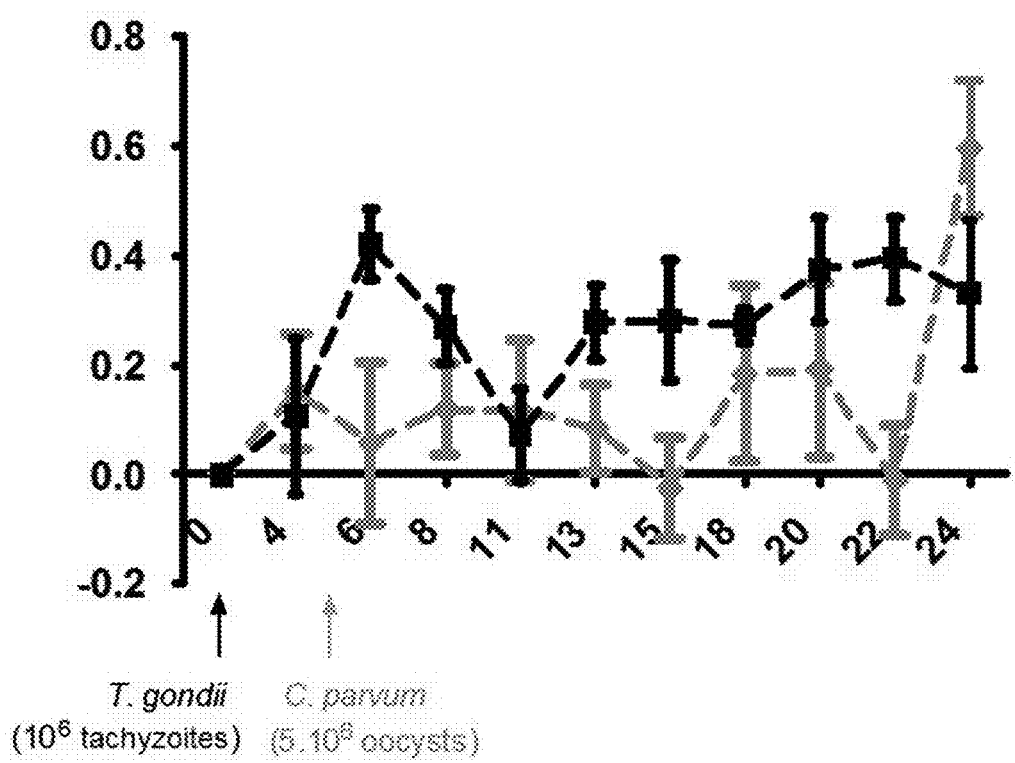

FIG. 18: illustrates the daily weight gain of lambs immunostimulated with $10^6$ tachyzoites Toxo mic1-3 KO, one day after their birth and challenged with $5.10^6$ oocysts of *C. parvum* (black square) and the control lambs only challenged (grey diamond).

on the x-axis: the time elapsed after stimulation of the lambs by Toxo mic1-3 KO (in days)

on the y-axis: the weight change of the lambs (in kg).

The average weight gain (DAG, daily average gain) reflects the rate of increase as a function of time according to the formula: DAG weight=d Weight/d' Age.

Figure 19:
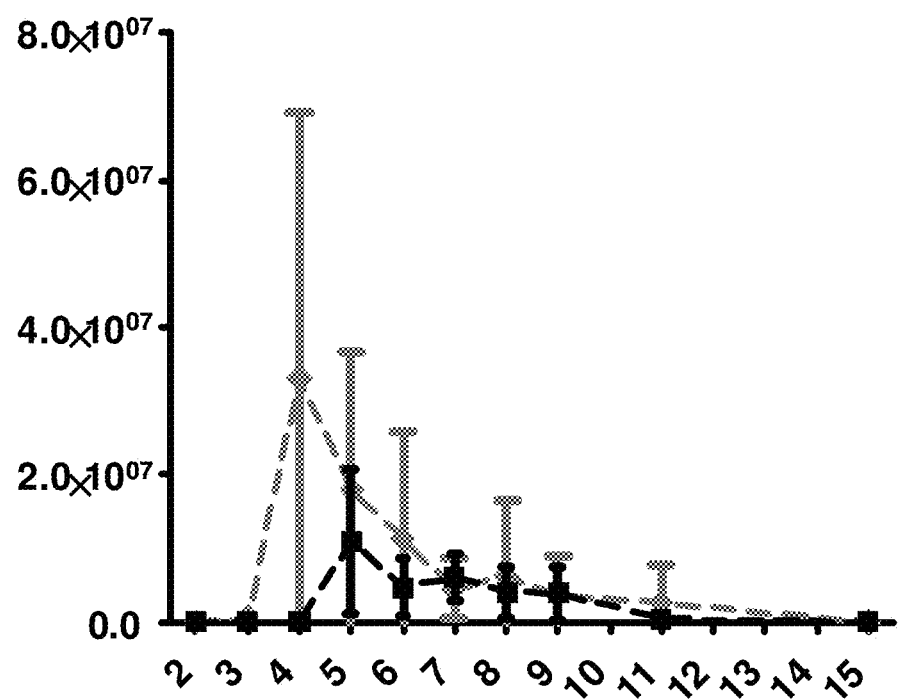

FIG. 19: illustrates the mean excretion of oocysts *C. parvum* per gram of excrement of lambs immunostimulated with $10^6$ tachyzoites Toxo mic1-3 KO, one day after their birth and challenged with $5.10^6$ oocysts of *C. parvum* (black square) and the control lambs only challenged (grey diamond).

on the x-axis: the time elapsed after infection of the lambs by *C. parvum* (in days)

on the y-axis: number of oocysts of *C. parvum* per gram of excrement.

EXPERIMENTAL SECTION

Figure 1:
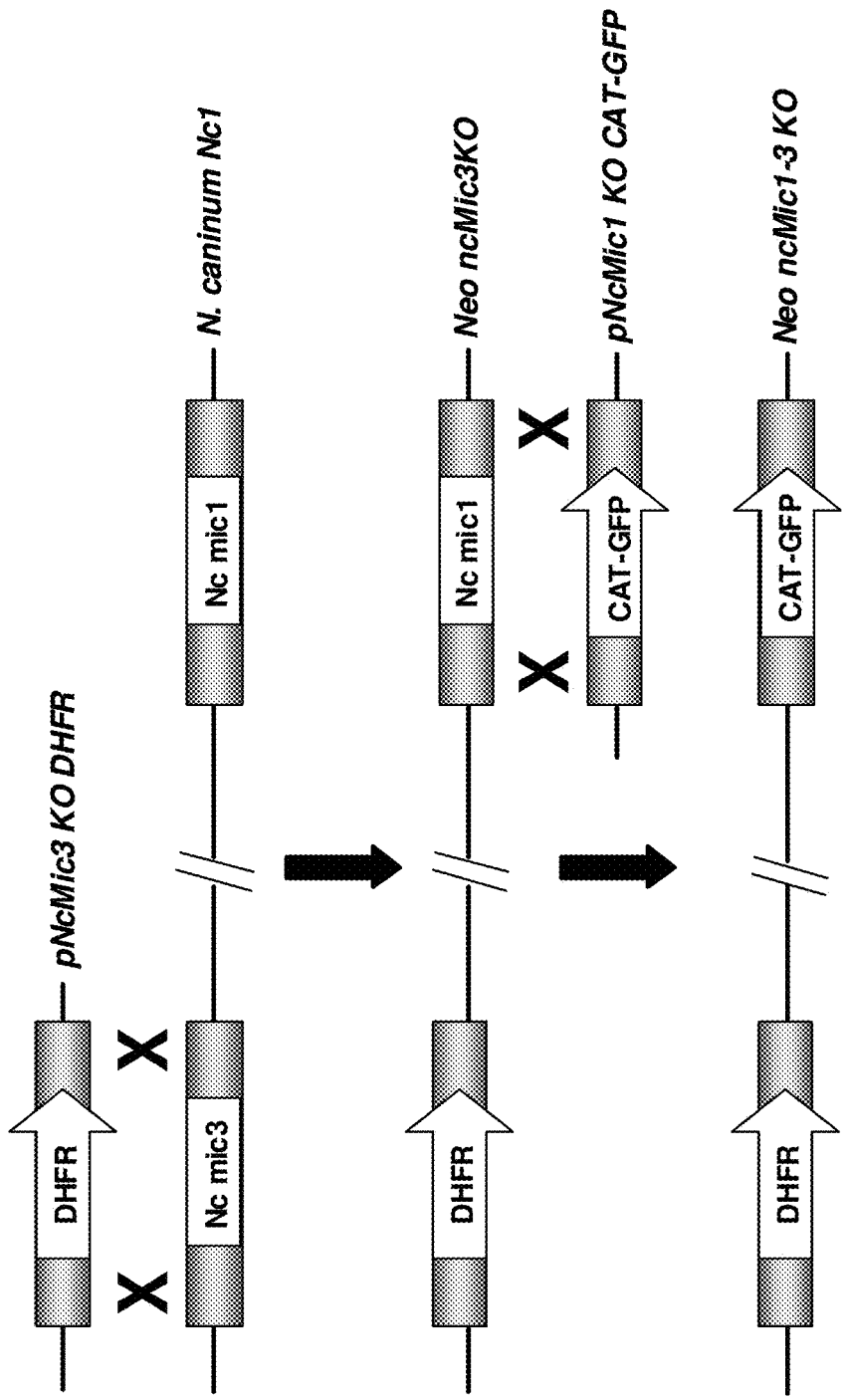
FIG. 1: this figure illustrates the 2 steps of homologous recombination in order to obtain the strain Neo ncmic1-3 KO. The first step of homologous recombination allows integration of the gene coding for the enzyme dihydrofolate reductase (DHFR) at the locus of the ncmic3 gene. Selection with pyrimethamine makes it possible to amplify the mutant single strain Neo ncmic3 KO. The Neo ncmic3 KO strain thus obtained serves for the second step of homologous recombination, which allows the integration of the gene coding for the chimeric protein chloramphenicol-acetyl-transferase/green fluorescent protein (CAT-GFP) at the locus of the ncmic1 gene. Selection with chloramphenicol then makes it possible to amplify the double mutant strain Neo ncmic1-3 KO.

In order to prepare the strain of *N. caninum* with the ncmic1 and ncmic3 genes knocked out, two steps of homologous recombination were carried out. The first step of homologous recombination makes it possible to obtain a simple mutant KO (strain Neo ncmic3 KO). The second step of homologous recombination is carried out in the strain Neo ncmic3 KO in order to obtain a doubly deleted strain (Neo ncmic1-3 KO) (FIG. 1).

Example 1

Construction of the Mutant Strain Neo ncmic3 KO

The haploidy of the genome of *Neospora caninum* during the proliferative phase allows inactivation of a gene in a single homologous recombination.

All the tachyzoites of the strain NC1 of *Neospora caninum* used were produced in human fibroblasts (HFF) cultured in Dulbecco's minimum medium (DMEM) supplemented with 10% of foetal calf serum (FCS), 2 mM of glutamine, 50 U/mL of penicillin and 50 μg/mL of streptomycin. They were harvested after mechanical lysis of the host cells and 3 passes through a 25G syringe.

a) Construction of the Plasmid pNcMic3KO-DHFR

The plasmid pNcMic3KO-DHFR (FIG. 2-A) contains the DHFR (dihydrofolate reductase) selection gene, which confers resistance to pyrimethamine. The DHFR selection gene is placed under the control of the α-tubulin promoter of *Toxoplasma gondii* (aTUB5 promoter) to allow expression of the gene in the parasite. The efficacy of this heterologous promoter had been demonstrated beforehand in *N. caninum*. This cassette is framed by the homologous regions (5HR-NcMic3 and 3HR-NcMic3) of the sequences flanking the ncmic3 gene. The DHFR selection cassette makes it possible to carry out selection for pyrimethamine.

The 5'UTR region of the ncmic3 gene was amplified by PCR from the genomic DNA of the strain NC1 of *Neospora caninum*. For the amplification, the primers 5 HR NCmic3 F KpnI and 5 HR NCmic3 R ClaI (SEQ ID NO: 1 and SEQ ID NO: 2) allow amplification of the 5'UTR region of the ncmic3 gene and creation of two restriction sites, which were used for cloning the 5HR fragment upstream of the DHFR selection cassette into the plasmid pT230 DHFR (KpnI at 5' and ClaI at 3' of the PCR fragment).

The 3'UTR region of the ncmic3 gene was amplified by PCR from the genomic DNA of the strain NC1 of *Neospora caninum*. For the amplification, the primers 3 HR NCmic3 F XbaI and 3 HR NCmic3 R NotI (SEQ ID NO: 3 and SEQ ID NO: 4) allow amplification of the 3'UTR region of the ncmic3 gene and creation of two restriction sites, which were used for cloning the 3HR fragment downstream of the DHFR selection cassette in the plasmid pT230 5HR-Nc-Mic3-DHFR (XbaI at 5' and NotI at 3' of the PCR fragment). The sequences of the primers are shown in Table I below.

TABLE I

List of the primers used for integration of the 5'UTR and 3'UTR sequences of the ncmic3 gene. The sequences of the restriction sites are underlined.

| Name of the primer | 5' → 3' Sequence | No. of sequence |
|---|---|---|
| 5 HR NCmic3 F KpnI | CGC<u>GGTACC</u>CATGTGAATATGCTTTAACCGTGAC | SEQ ID NO: 1 |
| 5 HR NCmic3 R ClaI | CGC<u>ATCGAT</u>GAGCTATAACCCTTGGAAATGACTC | SEQ ID NO: 2 |
| 3 HR NCmic3 F XbaI | CGC<u>TCTAGA</u>CATGCTGATGAAGAAGGGAAGT | SEQ ID NO: 3 |

TABLE I-continued

List of the primers used for integration of the 5'UTR and 3'UTR sequences of the ncmic3 gene. The sequences of the restriction sites are underlined.

| Name of the primer | 5' → 3' Sequence | No. of sequence |
|---|---|---|
| 3 HR NCmic3 R NotI | CGCGCGGCCGCTCTCTCCTGAAGTCTTCGAGACC | SEQ ID NO: 4 | b) Conditions for Electroporation and Selection

50 µg of the plasmid pNcMic3KO-DHFR, purified and then linearized by NotI, was added to $5 \times 10^7$ NC1 tachyzoites of *Neospora caninum* suspended in the CYTO-MIX electroporation medium containing ATP (3 mM) and glutathione (3 mM) (Van den Hoff et al., *Nucleic Acid Research*, June 11; 20(11): 2902), and electroporation was carried out in a cuvette with a 4 mm gap, in a volume of 800 µL on a BioRad apparatus (parameters: 2000 V, 50 ohms, 25 µF, with two electric shocks).

After electroporation, the tachyzoites were deposited on a monolayer of HFF cells in culture. For selection of the mutants, the culture medium is replaced and supplemented with the selection agent (2 µM pyrimethamine), 24 h after electroporation. Three culture passages are carried out in this medium.

After 16 days of selection, the resistant parasites are cloned by limit dilution in the wells of 96-well plates of HFF cells. After amplification, the lysis plaques caused by the parasite are investigated. The parasites are subcultured and their genomic DNA is extracted for PCR analyses. These PCR analyses should confirm integration of the transgene but should also allow differentiation of the parasites that have randomly integrated the transgene from the parasites of interest the ncmic3 gene of which has been effectively suppressed by homologous recombination.

c) PCR Analysis

Starting from the genomic DNA, PCRs were carried out for:

- investigating the size of the DNA fragment amplified with a set of PCR primers No. 1: HR NCmic3 F (SEQ ID NO: 5) and HR NCmic3 R (SEQ ID NO: 6), present on the homologous sequences. With random integration of the transgene, two DNA fragments of 2163 bp and of 3824 bp are amplified, whereas with homologous recombination, only a fragment of 3824 bp is amplified. With the wild-type strains, only a fragment of 2163 bp is amplified.
- verifying the presence/absence of the ncmic3 gene with the set of PCR primers No. 2: ORF NCmic3 F (SEQ ID NO: 7) and ORF NCmic3 R (SEQ ID NO: 8).
- and/or verifying the presence/absence of the DHFR cassette with the set of PCR primers No. 3: ORF DHFR F (SEQ ID NO: 9) and ORF DHFR R (SEQ ID NO: 10).

The sequences of the primers and the size of the amplicons resulting from the different PCRs are shown in Table II and Table III below, respectively.

TABLE II

List of the primers used for the different PCRs for validation of the construction of the mutant strain Neo ncmic3 KO.

| Name of the primer | 5' → 3' Sequence | No. of sequence | No. of PCR |
|---|---|---|---|
| HR NCmic3 F | GTCATCGACCGCCGGAACTAGTAGT | SEQ ID NO: 5 | 1 |
| HR NCmic3 R | GCAGAGGTTCTGCGTATCTAACACGG | SEQ ID NO: 6 | 1 |
| ORF NCmic3 F | TTTCCCTTCTAAACACAGTCG | SEQ ID NO: 7 | 2 |
| ORF NCmic3 R | CCTTCAGTGGTTCTCCATGAGT | SEQ ID NO: 8 | 2 |
| ORF DHFR F | CCTTCTCAGACAACGGGGTA | SEQ ID NO: 9 | 3 |
| ORF DHFR R | AGATCTTCACGCCCTTCTCA | SEQ ID NO: 10 | 3 |
| Integ NCmic3 F | GAAAGTGTCAGTGGTAGAGACTGC | SEQ ID NO: 11 | 4 and 6 |
| ORF NCmic3 R2 | CCTTCACTCGAGATCGCGCAAATGAGC | SEQ ID NO: 12 | 4 |
| ORF DHFR R2 | GGACCTCTGTACGAGACATGCCG | SEQ ID NO: 13 | 6 |
| Integ NCmic3 R | TGTTTACAGGTGATCCAGAAAAGG | SEQ ID NO: 14 | 5 and 7 |
| ORF NCmic3 F2 | GAATTTTGGGACAGGGGAAT | SEQ ID NO: 15 | 5 |
| ORF DHFR F2 | GTCTCTCGTTTTCCTCTCTTTTCGG | SEQ ID NO: 16 | 7 |

TABLE III

Size of the amplicons (in base pairs) of the different PCRs for validation
of the construction of the mutant strain Neo ncmic3 KO.

| No. of PCR | Neo ncmic3 KO | Neospora caninum (NC1) |
|---|---|---|
| 1 | 3824 | 2163 |
| 2 | — | 850 |
| 3 | 504 | — |
| 4 | — | 3127 |
| 5 | — | 3374 |
| 6 | 2890 | — |
| 7 | 3258 | — |

The electrophoretic profiles of the PCR products are presented in FIG. 3-A. Among the clones studied, certain clones display a specific band of DHFR (PCR 3) but no specific band of ncmic3 (PCR 2). PCR No. 1, which was carried out on these clones, revealed a band of 3824 bp specific for a Neo ncmic3 KO clone.

New PCR analyses were carried out on these clones of interest with new sets of primers. These PCRs, called integration PCRs, allow validation of the genetic KO using a primer present on the genome upstream or downstream of the sequences flanking the ncmic3 gene and a second primer present in the selection cassette (dhfr gene) or in the gene of interest (ncmic3) (FIG. 3-B).

In FIG. 3-B, PCRs No. 4 and No. 5 make it possible to show the presence of ncmic3 at the locus of ncmic3. PCR No. 4 is carried out with the primer set Integ NCmic3 F (SEQ ID NO: 11) and ORF NCmic3 R2 (SEQ ID NO: 12). PCR No. 5 is carried out with the primer set Integ NCmic3 R (SEQ ID NO: 14) and ORF NCmic3 F2 (SEQ ID NO: 15). The presence of bands for the wild-type strain NC1 of Neospora caninum and the absence of these bands for the mutant strain Neo ncmic3 KO are observed. In FIG. 3-B, PCRs No. 6 and No. 7 make it possible to show the presence of DHFR at the locus of ncmic3. PCR No. 6 is carried out with the primer set Integ NCmic3 F (SEQ ID NO: 11) and ORF DHFR R2 (SEQ ID NO: 13). PCR No. 7 is carried out with the primer set Integ NCmic3 R (SEQ ID NO: 14) and ORF DHFR F2 (SEQ ID NO: 16). The absence of bands for the wild-type strain NC1 of Neospora caninum and the presence of bands for the strain Neo ncmic3 KO are noted. The presence of a non-specific band for PCR No. 6 at approximately 1000 bp should be noted.

All of the PCR results demonstrate that homologous recombination has indeed taken place and that ncmic3 gene has indeed been deleted from the mutant strain Neo ncmic3 KO.

d) Analysis by Immunofluorescence

Analysis was carried out by immunofluorescence. 24 h before immunofluorescence analysis, $5 \times 10^5$ parasites were deposited in a p24 well containing a coverslip covered with a HFF cell lawn.

The cells infected by the parasites are washed twice with 1×PBS and then fixed with paraformaldehyde (3.7% in 1×PBS) for 30 min. After 3 washings with 1×PBS, the cells are permeabilized with Triton solution (0.1% in 1×PBS) for 5 minutes. After 3 washings with 1×PBS, a saturation step is carried out with a solution of 1×PBS/10% FCS (foetal calf serum) for 30 min. The cells are then incubated with the primary antibody diluted in a solution of PBS/2% FCS (foetal calf serum) for 1 hour, washed 3 times and then incubated with the secondary antibody diluted in a solution of PBS/2% FCS (foetal calf serum) for 1 hour. After 2 washings with 1×PBS, the coverslips are mounted on a slide with Immu-Mount and are observed with a fluorescence microscope.

The primary antibody used is an antibody that allows detection of expression of the protein NcMIC3 in the parasite (primary antibody: rabbit anti-mica antibody and commercial secondary antibody: Alexa Fluor® 594 goat anti-rabbit, Life Technologies ref. A-11012).

For the wild-type strain NC1 of Neospora caninum, red fluorescence is observed at the apical pole of the parasite, revealing the presence of the protein NcMIC3 (FIG. 0508-1387-4A), whereas for the mutant strain Neo ncmic3 KO, no fluorescence is observed at the apical pole of the parasite, demonstrating absence of the protein NcMIC3 (FIG. 4B).

Example 2

Construction of the Mutant Strain Neo ncmic1 KO a) Construction of the Plasmid pNc mic1KO-CAT-GFP The plasmid pNcMic1KO-CAT-GFP (FIG. 2-B) contains a CAT-GFP selection cassette coding for a fusion protein giving both resistance to chloramphenicol (CAT) and green fluorescence (GFP: Green Fluorescent Protein). The latter is placed under the control of the α-tubulin promoter of Toxoplasma gondii to allow expression of the gene in the parasite. Either side of the cassette, the homologous regions of the sequences flanking the ncmic1 gene have been cloned.

The 3' UTR region of the ncmic1 gene was amplified by PCR from the genomic DNA of the strain NC1 of Neospora caninum. For the amplification, the primers 3 HR NCmic1 F KpnI and 3 HR NCmic1 R HindIII (SEQ ID NO: 17 and SEQ ID NO: 18) allow amplification of the 3'UTR region of the ncmic1 gene and creation of two restriction sites, which were used for cloning the 3HR fragment upstream of the CAT-GFP selection cassette into the plasmid pT230 CAT-GFP (KpnI at 5' and HindIII at 3' of the PCR fragment). The 5' UTR region of the ncmic1 gene was amplified by PCR from the genomic DNA of the strain NC1 of Neospora caninum. For the amplification, the primers 5 HR NCmic1 F BamHI and 5 HR NCmic1 R NotI (SEQ ID NO: 19 and SEQ ID NO: 20) allow amplification of the 5' UTR region of the ncmic1 gene and creation of two restriction sites, which were used for cloning the 5HR fragment downstream of the CAT-GFP selection cassette into the plasmid pT230 3HRNcMic1CAT-GFP (BamHI at 5' and NotI at 3' of the PCR fragment). The sequences of the primers are shown in Table IV below.

TABLE IV

List of the primers used for integration of the 5'UTR and 3'UTR
sequences of the ncmic 1 gene. The sequences of the restriction
sites are underlined.

| Name of the primer | 5' → 3' Sequence | No. of sequence |
|---|---|---|
| 3 HR NCmic1 F KpnI | CGCGGTACCAGGCAGAAGTAAAGAAGGTTCCTC | SEQ ID NO: 17 |

TABLE IV-continued

List of the primers used for integration of the 5'UTR and 3'UTR sequences of the ncmic 1 gene. The sequences of the restriction sites are underlined.

| Name of the primer | 5' → 3' Sequence | No. of sequence |
|---|---|---|
| 3 HR NCmic1 R HindIII | CGCAAGCTTTGATCACGCAAGAAA AGAAGC | SEQ ID NO: 18 |
| 5 HR NCmic1 F BamHI | CGCGGATCCCATTTGTAGATACGGT TGCACAC | SEQ ID NO: 19 |
| 5 HR NCmic1 R NotI | CGCGCGGCCGCACATTCAGACGGC AGAACTCTG | SEQ ID NO: 20 | b) Conditions for Electroporation and Selection

50 µg of the plasmid pNcMic1KO-CAT-GFP, purified and then linearized by KpnI, must be added to $5\times10^7$ NC1 tachyzoites suspended in CYTOMIX electroporation medium containing ATP (3 mM) and glutathione (3 mM) (Van den Hoff et al., *Nucleic Acid Research*, June 11; 20(11): 2902), and electroporation must be carried out in a cuvette with a 4 mm gap, in a volume of 800 µL on a BioRad apparatus (parameters: 2000 V, 50 ohms, 25 µF, with two electric shocks).

After electroporation, the tachyzoites will be deposited on a monolayer of HFF cells in culture. For selection of the mutants, the culture medium will be replaced and supplemented with the selection agent (50 µM chloramphenicol), 24 h after electroporation. Three culture passages must be carried out in this medium.

After 15 days of selection, the resistant parasites will be cloned by limiting dilution in the wells of 96-well plates of HFF cells. After amplification, the lysis plaques caused by the parasite will be investigated. The parasites will be subcultured and their genomic DNA will be extracted for PCR analyses.

c) PCR Analysis

The sequences of the primers and the expected size of the amplicons resulting from the different PCRs are shown in Table V and Table VI below, respectively.

TABLE V

List of the primers used for the different PCRs for validation of the construction of the mutant strains Neo ncmic1 KO.

| Name of the primer | 5' → 3' Sequence | No. of sequence | No. of PCR |
|---|---|---|---|
| Integ NCmic1 F | CCGAGCAAGTTAGCAAGTCC | SEQ ID NO: 21 | 1 and 3 |
| ORF CATGFP R | CCGTTTGGTGGATGTCTTCT | SEQ ID NO: 22 | 1 |
| ORF CATGFP F | GCATCGACTTCAAGGAGGAC | SEQ ID NO: 23 | 2 |
| Integ NCmic1 R | CTTGTCCGTCACATCGTTTG | SEQ ID NO: 24 | 2 and 4 |
| ORF NCmic1 R | TTCTCCAGGCACTCACCTCT | SEQ ID NO: 25 | 3 |
| ORF NCmic1 F | AGCTTCCAACAACGAGAGGA | SEQ ID NO: 26 | 4 |
| ORF NCmic1 F2 | CCCAGGATATCGTTTGTTGC | SEQ ID NO: 27 | 5 |
| ORF NCmic1 R2 | CTTCTGATGCACGGAACTGA | SEQ ID NO: 28 | 5 |
| ORF CATGFP F2 | CCTGAAGTTCATCTGCACCA | SEQ ID NO: 29 | 6 |
| ORFCATGFP R2 | GTAGTGGTTGTCGGGCAGCA | SEQ ID NO: 30 | 6 |

TABLE VI

Size of the amplicons (in base pairs) of the different PCRs for validation of the construction of the mutant strain Neo ncmic1 KO.

| No. of PCR | Neo ncmic1 KO | *Neospora caninum* (NC1) |
|---|---|---|
| 1 | 3359 | — |
| 2 | 3421 | — |
| 3 | — | 3746 |
| 4 | — | 3046 |
| 5 | — | 449 |
| 6 | 472 | — |

Example 3

Construction of the Mutant Strain Neo ncmic1-3 KO a) Construction of the plasmid pNc mic1KO-CAT-GFP Construction of the plasmid pNcMic1KO-CAT-GFP is described in Example 2 (2a).

b) Conditions for Electroporation and Selection

50 µg of the plasmid pNcMic1KO-CAT-GFP, purified and then linearized by KpnI, was added to $5\times10^7$ Neo ncmic3 KO tachyzoites suspended in the CYTOMIX electroporation medium containing ATP (3 mM) and glutathione (3 mM) (Van den Hoff et al., *Nucleic Acid Research*, June 11; 20(11): 2902), and electroporation was carried out in a cuvette with a 4 mm gap, in a volume of 800 μL on a BioRad apparatus (parameters: 2000 V, 50 ohms, 25 μF, with two electric shocks).

After electroporation, the tachyzoites were deposited on a monolayer of HFF cells in culture. For selection of the mutants, the culture medium is replaced and supplemented with the selection agent (chloramphenicol 50 μM), 24 h after electroporation. Three culture passages are carried out in this medium.

After 15 days of selection, the resistant parasites are cloned by limiting dilution in the wells of 96-well plates of HFF cells. After amplification, the lysis plaques caused by the parasite are investigated. The parasites are subcultured and their genomic DNA is extracted for PCR analyses.

c) PCR Analysis

The sequences of the primers and the size of the amplicons resulting from the different PCRs are shown in Table VII and Table VIII below, respectively.

TABLE VIII

Size of the amplicons (in base pairs) of the different PCRs for validation of the construction of the mutant strains Neo ncmic3 KO and Neo ncmic1-3 KO.

| No. of PCR | Neo ncmic1-3 KO | *Neospora caninum* (NC1) | Neo ncmic3 KO |
|---|---|---|---|
| 1 | 3359 | — | — |
| 2 | 3421 | — | — |
| 3 | — | 3746 | 3746 |
| 4 | — | 3046 | 3046 |
| 5 | — | 3127 | — |
| 6 | — | 3374 | — |
| 7 | 2890 | — | 2890 |
| 8 | 3258 | — | 3258 |
| 9 | — | 449 | 449 |
| 10 | 472 | — | — |
| 11 | — | 850 | — |
| 12 | 504 | — | 504 |

Figure 5:
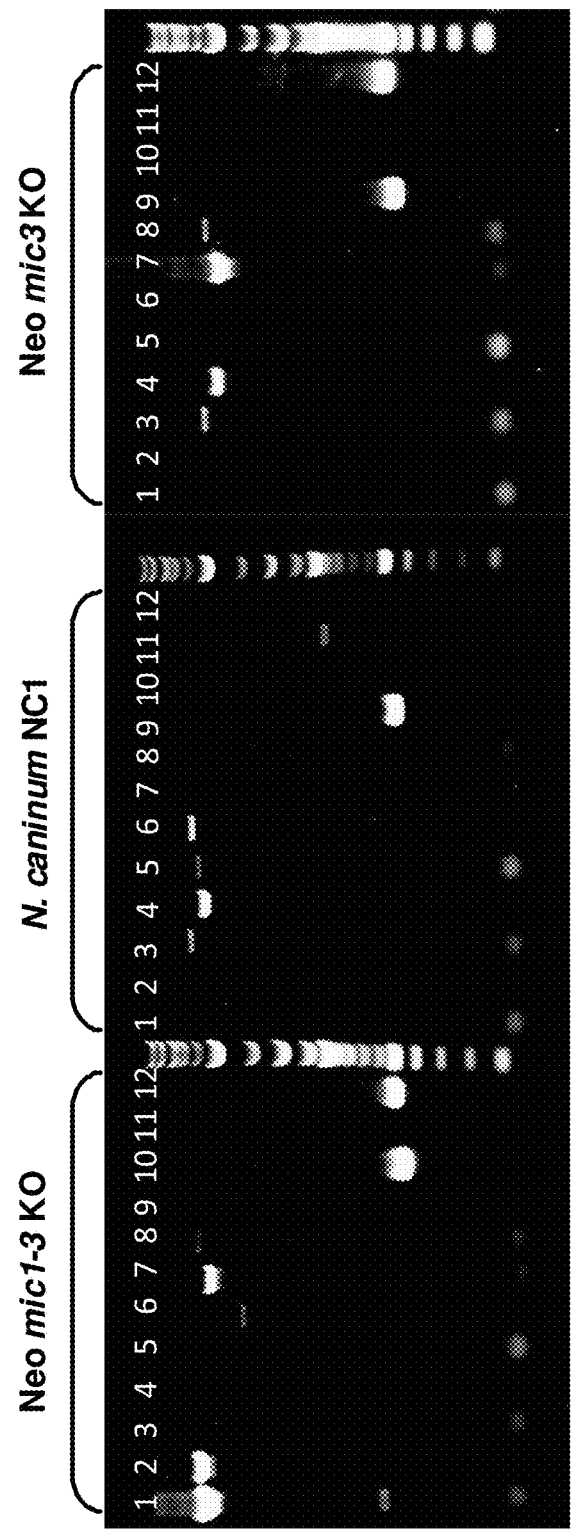
FIG. 5: this figure shows the electrophoretic profiles of the PCR products obtained respectively in the wild-type strain NC1 of *N. caninum*, in the mutant strain Neo ncmic3 KO and in the mutant strain Neo ncmic1-3 KO using the sets of PCR primers No. 1 to No. 12 in Table VII which correspond to SEQ ID NO: 7 to 16 and to SEQ ID NO: 21 to 30.

In FIG. 5, PCR No. 1 is carried out with the set of primers Integ NCmic1 F (SEQ ID NO: 21) and ORF CATGFP R

TABLE VII

List of the primers used for the different PCRs for validation of the construction of the mutant strains Neo ncmic3 KO and Neo ncmic1-3 KO.

| Name of the primer | 5' → 3' Sequence | No. of sequence | No. of PCR |
|---|---|---|---|
| Integ NCmic1 F | CCGAGCAAGTTAGCAAGTCC | SEQ ID NO: 21 | 1 and 3 |
| ORF CATGFP R | CCGTTTGGTGGATGTCTTCT | SEQ ID NO: 22 | 1 |
| ORF CATGFP F | GCATCGACTTCAAGGAGGAC | SEQ ID NO: 23 | 2 |
| Integ NCmic1 R | CTTGTCCGTCACATCGTTTG | SEQ ID NO: 24 | 2 and 4 |
| ORF NCmic1 R | TTCTCCAGGCACTCACCTCT | SEQ ID NO: 25 | 3 |
| ORF NCmic1 F | AGCTTCCAACAACGAGAGGA | SEQ ID NO: 26 | 4 |
| Integ NCmic3 F | GAAAGTGTCAGTGGTAGAGACTGC | SEQ ID NO: 11 | 5 and 7 |
| ORF NCmic3 R2 | CCTTCACTCGAGATCGCGCAAATGAGC | SEQ ID NO: 12 | 5 |
| ORF DHFR R2 | GGACCTCTGTACGAGACATGCCG | SEQ ID NO: 13 | 7 |
| Integ NCmic3 R | TGTTTACAGGTGATCCAGAAAAGG | SEQ ID NO: 14 | 6 and 8 |
| ORF NCmic3 F2 | GAATTTTGGGACAGGGGAAT | SEQ ID NO: 15 | 6 |
| ORF DHFR F2 | GTCTCTCGTTTTCCTCTCTTTTCGG | SEQ ID NO: 16 | 8 |
| ORF NCmic1 F2 | CCCAGGATATCGTTTGTTGC | SEQ ID NO: 27 | 9 |
| ORF NCmic1 R2 | CTTCTGATGCACGGAACTGA | SEQ ID NO: 28 | 9 |
| ORF CATGFP F2 | CCTGAAGTTCATCTGCACCA | SEQ ID NO: 29 | 10 |
| ORFCATGFP R2 | GTAGTGGTTGTCGGGCAGCA | SEQ ID NO: 30 | 10 |
| ORF NCmic3 F | TTTCCCTTCTAAACACAGTCG | SEQ ID NO: 7 | 11 |
| ORF NCmic3 R | CCTTCAGTGGTTCTCCATGAGT | SEQ ID NO: 8 | 11 |
| ORF DHFR F | CCTTCTCAGACAACGGGGTA | SEQ ID NO: 9 | 12 |
| ORF DHFR R | AGATCTTCACGCCCTTCTCA | SEQ ID NO: 10 | 12 |

(SEQ ID NO: 22). PCR 2 is carried out with the set of primers ORF CATGFP F (SEQ ID NO: 23) and Integ NCmic1 R (SEQ ID NO: 24). PCR No. 3 is carried out with the set of primers Integ NCmic1 F (SEQ ID NO: 21) and ORF NCmic1 R (SEQ ID NO: 25). PCR No. 4 is carried out with the set of primers Integ NCmic1 R (SEQ ID NO: 24) and ORF NCmic1 F (SEQ ID NO: 26). PCR No. 5 is carried out with the set of primers Integ NCmic3 F (SEQ ID NO: 11) and ORF NCmic3 R2 (SEQ ID NO: 12). PCR No. 6 is carried out with the set of primers Integ NCmic3 R (SEQ ID NO: 14) and ORF NCmic3 F2 (SEQ ID NO: 15). PCR No. 7 is carried out with the set of primers Integ NCmic3 F (SEQ ID NO: 11) and ORF DHFR R2 (SEQ ID NO: 13). PCR No. 8 is carried out with the set of primers Integ NCmic3 R (SEQ ID NO: 14) and ORF DHFR F2 (SEQ ID NO: 16). PCR No. 9 is carried out with the set of primers ORF NCmic1 F2 (SEQ ID NO: 27) and ORF NCmic1 R2 (SEQ ID NO: 28). PCR No. 10 is carried out with the set of primers ORF CATGFP F2 (SEQ ID NO: 29) and ORF CATGFP R2 (SEQ ID NO: 30). PCR No. 11 is carried out with the set of primers ORF NCmic3 F (SEQ ID NO: 7) and ORF NCmic3 R (SEQ ID NO: 8). PCR No. 12 is carried out with the set of primers ORF DHFR F (SEQ ID NO: 9) and ORF DHFR R (SEQ ID NO: 10).

The electrophoretic analyses of the PCR products show that the strain Neo ncmic1-3 KO no longer has the ncmic1 and ncmic3 genes (wells 3, 4, 5, 6, 9 and 11, FIG. 5) and does have the dhfr and cat-gfp genes (wells 1, 2, 7, 8, 10 and 12, FIG. 5), thus validating production of the strain Neo ncmic1-3 KO. All of the PCR results demonstrate that homologous recombination has indeed taken place and the strain Neo ncmic1-3 KO has indeed been deleted from the ncmic1 and ncmic3 genes.

d) Immunofluorescence Analysis

Figure 6:
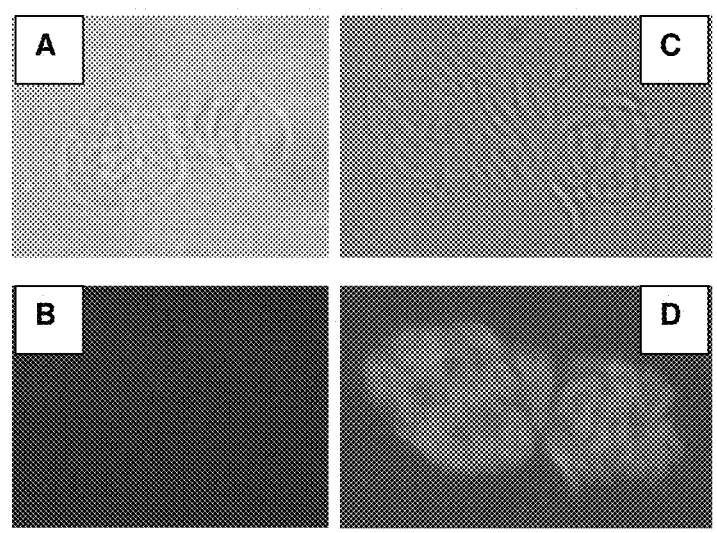
FIG. 6: this figure illustrates the analysis for detecting the GFP protein in the mutant strains Neo ncmic3 KO (images A and B) and Neo ncmic1-3 KO (image C and D) by immunofluorescence, using the fluorescent properties of the CAT-GFP protein. One and the same microscopic field is visualized in direct light (top images A and C) or in fluorescence (bottom images B and D).

Immunofluorescence analysis was carried out solely by direct observation of the fluorescence of the parasite (FIG. 6).

The parasites of the two mutant strains are visualized in direct light (images A and C). One and the same microscopic field is visualized in fluorescence. Green fluorescence, due to expression of the recombinant chimeric protein CAT-GFP, is only detected in the mutant strain Neo ncmic1-3 KO (image D) following insertion of the CAT-GFP cassette. Conversely, the strain Neo ncmic3 KO, which does not have a CAT-GFP cassette, does not express the CAT-GFP protein and consequently does not display fluorescence (image B).

Example 4

Immunostimulation of the Mouse Pups with the Mutant Toxo mic1-3 KO

1—Experimental Protocol
  1.1—Animals

Immunostimulation is carried out on the C57BL/6 mouse pups aged 3 days. These mouse pups were obtained and bred in the INRA Centre in Nouzilly (Indre et Loire, France). The mouse pups are kept throughout the experiments in an animal house of containment level 2 in order to minimize the risk of external contamination.
  1.2—Strain *T. gondii*
    1.2.1—Strain Toxo mic1-3 KO The mutant strain of *Toxoplasma gondii*, in which the genes coding for the proteins MIC1 and MIC3 were knocked out (called strain Toxo mic1-3 KO) is maintained by successive passages on a human foreskin fibroblast (HFF) line cultured in DMEM medium supplemented with 10% of foetal calf serum (FCS), 2 mM of glutamine, 50 U/mL of penicillin and 50 µg/mL of streptomycin.
    1.2.2—Strain RH The wild-type strain RH of *Toxoplasma gondii*, from which the strain Toxo mic1-3 KO is derived, is also maintained by successive passages on a human foreskin fibroblast (HFF) line cultured in DMEM medium supplemented with 10% of foetal calf serum (FCS), 2 mM of glutamine, 50 U/mL of penicillin and 50 µg/mL of streptomycin.

For preparation of the total parasite extract, the tachyzoites of the strain RH are washed, sonicated at 60 W/s, three times for 10 min and centrifuged at 2000 g for 30 min at 4° C. The supernatant is concentrated and divided into aliquots. The concentration is determined by BCA assay, using BSA (Bovine Serum Albumin) as standard. The aliquots are stored at −20° C.
  1.3—Immunostimulation Batches of 3-day-old C57BL/6 mouse pups were treated as follows:
  6 mouse pups (batch A) served as unvaccinated control batch,
  6 mouse pups (batch B) received the mutant Toxo mic1-3 KO On D0, the mouse pups in batch A received 20 tachyzoites of the strain Toxo mic1-3 KO by intraperitoneal route.

On D3 post-immunostimulation, 3 mouse pups from each batch were sacrificed for investigating the humoral immune response, the inflammatory response and parasitaemia.

On D9 post-immunostimulation, the 3 remaining mouse pups of each batch were sacrificed for investigating the humoral immune response, the inflammatory response and parasitaemia.
  1.4—Humoral Immune Response The humoral immune response was studied by evaluating, by ELISA, the kinetics of appearance of the IgM specific anti-*Toxoplasma gondii* antibodies in the serum. The sera are taken at the moment of sacrifice of the mouse pups on D3 and on D9 post-infection. The sample is left for 10 min at room temperature to allow clotting. The serum is recovered by centrifuging the samples at 2000 rpm for 10 min at +20° C. The supernatant is divided into aliquots in a clean tube and stored at −20° C.

The total extract of the RH strain of *Toxoplasma gondii*, obtained as described above, is used for sensitizing the flat-bottomed wells of microtitre plates (Nunc). 100 µL of extract (at a concentration of 10 µg/mL in carbonate buffer at 50 mM and pH=9.6) is deposited in each well. After one night at +4° C., three washings are carried out in PBS buffer with the addition of 0.05% Tween-20 (PBS-T).

The non-specific sites are saturated by incubation of the plates for 1.5 h at 37° C. under humid atmosphere with PBS with 4% BSA.

100 µL of each sample of serum diluted in PBS-T (1/50 dilution) is deposited and incubated for 1 h at 37° C. under humid atmosphere.

After two series of three washings, 100 µL of anti-mouse IgM coupled to alkaline phosphatase (ALP; Sigma), diluted to 1/5000 in PBS-T, is deposited and incubated for 1.5 h at 37° C. under humid atmosphere. Two new series of three washings are carried out. Development is carried out using 100 µL of paranitrophenylphosphate (PNPP) at 1 mg/mL in DEA-HCL.

Reading is carried out after incubation for 10 to 20 minutes, on a plate reader (Wallac 1420 Multilabel counter) at a wavelength $\lambda$=405 nm.

The assumed positivity threshold was determined as a function of the values of absorbance (OD) of the mouse pups in the control batch: it is fixed at 0.23 of OD for a 1/50 serum dilution.

1.5—Investigation of the Inflammatory Response

Analysis of the inflammatory response of the mouse pups at intestinal level was quantified by quantitative PCR (qPCR) by amplification of the genes coding for IL-12 and IFN-γ. IL-12 is a cytokine produced in response to intrusion of a pathogen that stimulates secretion of IFN-γ, a cytokine produced by the immune system cells in response to inflammation on the site of infection by the pathogen.

After sacrifice of the mouse pups on D3 and D9, the intestine is removed and the ileum (1 cm above the caecum) is used for analysis by qPCR. The tissue is incubated in 1 mL of Trizol® (Invitrogen) and then is ground in a Thurax, incubated at room temperature for 5 min and centrifuged for 10 minutes at 12,000 g. The supernatant is then recovered and mixed by pipetting up and down approximately ten times.

Once the nuclear protein complexes have been dissociated with Trizol®, the RNA is isolated from the DNA and from the proteins with chloroform. One millilitre of chloroform is added to the supernatant and the Trizol®/chloroform mixture is stirred vigorously for 15 seconds, then incubated at room temperature and finally centrifuged at 12,000 g for 15 minutes at 4° C. After centrifugation, the mixture is separated into an organic phase (phenol/chloroform, pink, lower phase), an interphase (white film, DNA and cell debris) and an aqueous phase (upper phase) containing the total RNAs.

The aqueous phase containing the total RNAs is recovered and 500 µL of isopropanol is added to precipitate the RNA. The solution is stirred, incubated at room temperature for 10 min. and centrifuged at 12,000 g for 10 min at 4° C. The pellet obtained is isolated and then washed with 1 mL of 75% ethanol (absolute ethanol diluted in 0.1% DEPC water and stored at −20° C.), stirred and centrifuged at 7500 g at 4° C. for 10 min. The pellet is dried for 10 min under a fume hood in ice. Finally the RNA is taken up in approximately 20 µL of 0.1% DEPC water.

The quality of extraction of the RNA is verified by electrophoresis on 1% agarose gel and by calculating the direct ratio of the absorbance at a wavelength of 260 nm to that at a wavelength of 280 nm. This ratio must be close to 2. Finally, the RNA extraction yield is quantified using a spectrophotometer.

Two micrograms of RNA are incubated with 1 µL, of Oligo dT (Eurogentec 133 pmol/µl) in a final volume of 11 µL, at 65° C. for 10 min, and then 2 min in ice. Once the oligonucleotides dT are fixed on the polyA tail, the RNA solution is incubated with 2 µL, of dNTP (dATP, dTTP, dGTP, dCTP each at 20 mM), 4 µL, of reverse transcriptase buffer (5× Eurogentec; 250 mM Tris-HCl (pH 8.3); 375 mM KCl; 50 mM DTT; 15 mM $MgCl_2$) and 0.4 µL of MuMLV (25 U/µL; 50 mM Tric-HCL (pH 8.3); 1 mM EDTA, 0.1% Triton X-100, 0.1 M NaCl; 5 mM DTT; 50% (v/v) glycerol) in a final volume of 20 µL, for 1.5 h at 37° C. The reverse transcriptase is then inhibited at 85° C. for 10 min.

In the present case, expression of the genes coding for the proteins IL-12 and IFN-γ, expressed during the inflammatory response, was quantified. For amplification, the primer pair SEQ ID NO: 31 (5'-CTCACATCTGCTGCTCCACAA-3') and SEQ ID NO: 32 (5'-GACGCCATTCCACATGT-CACT-3') was used for IL-12, the primer pair SEQ ID NO: (5'-TCTTCTTGGATATCTGGAGGAA-3') and SEQ ID NO: 34 (5'-AGCTCATTGAATGCTTGGCGCTG-3') was used for assaying IFNγ and the primer pair SEQ ID NO: 35 (5'-GGATACAGGCCAGACTTTGTTG-3') and SEQ ID NO: 36 (5'-GAGGGTAGGCTGGCCTATAG-3') was used for assaying the murine HPRT reference gene.

Two microlitres of cDNA diluted to 1/10 from the reverse transcription reaction is incubated with 0.3 µL of the 5' primer (25 µM); 0.3 µL, of the 3' primer (25 µM); 7.50 µL of Mix PCR (BioRad) in a final volume of 15 µL. The conditions selected for the PCR reaction are as follows: 1) denaturation at 95° C. for 5 minutes, 2) denaturation at 95° C. for 10 seconds, 3) pairing and elongation at 62° C. for IL-12, IFNγ and HPRT for 15 seconds, 4) repeating the cycle starting from step 2: 39 times, 5) melting curve from 55° C. to 95° C. to verify the presence or absence of the dimers.

1.6—Investigation of the State of Infection of the Mouse Pups

The level of infection of the mouse pups was analysed by three different techniques: 1) tissue dissemination of the tachyzoites on HFF cells, 2) immunohistology on sections of intestine from the infected mouse pups and 3) PCR from the ileum of the mouse pups in batches A and B.

1.6.1—Tissue Dissemination of the Tachyzoites on HFF Cells

The HFF cells are deposited in a 24-well plate one week before depositing the organs at a rate of $1 \times 10^4$ cells/well. The cells are cultured in 1 mL of DMEM cell culture medium supplemented with 10% of foetal calf serum (FCS), 2 mM of glutamine, 50 U/mL of penicillin and 50 µg/mL of streptomycin.

After sacrifice, the spleen of the mouse pups of batches 1 and 2 is removed and ground in 2 mL of 1×PBS. Ten microlitres of ground material is deposited per well containing the HFF cells. Twenty-four hours after depositing the ground materials from the spleen, the cells are washed with DMEM and then 1 mL of clean medium is deposited in each well. The cells are incubated at 37° C., 5% $CO_2$ until the lysis plaques revealing the presence of Toxo mic1-3 KO tachyzoites are detected.

1.6.2—Immunohistology on Sections of Intestine from the Infected Mouse Pups

The intestine of the sacrificed mouse pups is rolled up like a Swiss roll and then kept in this form using paper wrapped around the Swiss roll and stapled. The samples are fixed in 4% paraformaldhehyde solution, diluted in 1×PBS (pH=7) and incubated for 8 hours at 4° C. The tissues are then washed in 1×PBS and then incubated at 4° C. for 8 h in clean 1×PBS. This last step is repeated a second time. The tissues are incubated for 8 hours at 4° C., in 30% sucrose solution diluted in 1×PBS and filtered. Finally the tissues are transferred to moulds of a suitable size filled with OCT embedding medium. After 5 minutes of incubation in the OCT, the samples are frozen using dry ice and stored at −80° C.

The samples of intestine are then cut into sections using a cryostat which maintains the sample at −20° C. Histological sections with a thickness of 7 µm are prepared and then deposited on a slide by electrostatic force. The slides are stored at −80° C.

The slides of histological sections are thawed and then left to dry at room temperature for 1 h. The zone of the sample on the slide is delimited with a pen with hydrophobic ink (Dakocitamation pen). The histological sections of intestine are permeabilized with 50 µL of a solution of 1×PBS, $Mg^{2+}$, $Ca^{2+}$ free, Triton X-100 and 1% BSA at room temperature and in a humid chamber for 10 min. The permeabilizing solution is removed by aspiration and the samples are saturated in 50 µL of a solution of 1×PBS, $Mg^{2+}$, $Ca^{2+}$ free, Triton X-100 and 10% BSA at room temperature and in a humid chamber for 1 h. After aspiration of the saturation solution, 50 µL of rabbit anti-SAG1 polyclonal serum of *Toxoplasma gondii* diluted to 1/100 in a solution of 1×PBS, $Mg^{2+}$, $Ca^{2+}$ free, Triton X-100 and BSA 1%, is deposited per sample. The samples are incubated at 4° C., in a humid chamber for 8 h. Two washings for 5-minutes in 1×PBS, $Mg^{2+}$, $Ca^{2+}$ free, Triton X-100 and 1% BSA are carried out. 50 µL of swine anti-rabbit antibodies coupled to fluorescein isothiocyanate diluted to 1/20 in a solution of 1×, $Mg^{2+}$, $Ca^{2+}$ free, Triton X-100 and 1% BSA is deposited per sample. The samples are incubated in the presence of the coupled secondary antibody, at room temperature, in a humid chamber for 1 h 20 min Two washings for 5-minute in 1×PBS, $Mg^{2+}$, $Ca^{2+}$ free, Triton X-100 and 1% BSA are carried out and then a final washing of the samples is carried out in sterile distilled water. The slides are dried and then a drop of fluoromount G is deposited on each sample. Finally, the samples are mounted between the slide and the cover slip.

1.6.3—Detection of SAG-1

A PCR was carried out from cDNAs obtained by reverse transcription reaction (cf. paragraph 1.5). The SAG-1 gene specific to the parasite *Toxoplasma gondii* was amplified by PCR with the primers SEQ ID NO: 37 (5'-CTGCACCACT-TCATTATTTCTTCTG-3') and SEQ ID NO: 38 (5'-ACT-CACGCGACACAAGCTG-3').

2 µL, of cDNA is incubated with 1 µL of 5' primer (10 µM); 1 µL of 3' primer (10 µM); 250 µL of GoTaq®Green Master Mix (2×, Promega) in a final volume of 50 µL. The conditions selected for the PCR are as follows: 1) denaturation at 94° C. for 5 min, 2) denaturation at 94° C. for 30 s, 3) pairing at 60° C. for 30 s, 4) elongation at 72° C. for 1 min, 5) repeating the cycle starting from step 2: 34 times, 6) elongation at 72° C. for 5 min. The presence of the parasite *Toxoplasma gondii* in the intestine is verified by an amplified fragment of 1001 base pairs.

2—Results 2.1—Investigation of the Humoral Response Post-Immunostimulation

The results of the ELISA assays on D3 and D9 post-infection for the sera of the batches of mouse pups, controls and immunostimulated with the strain Toxo mic1-3 KO, are shown in FIG. 7. The mouse pups in the control batch (A) have not developed a humoral response on D3 and on D9 post-infection in contrast to 2 mouse pups out of 3 of the batch immunostimulated with the strain Toxo mic1-3 KO (B), which produced anti-toxoplasmic IgM antibodies at 9 days post-infection; these are the mouse pups No. 4 and No. 6.

2.2—Investigation of the Inflammatory Response Post-Immunostimulation

The results of the quantitative PCR tests for expression of the gene coding for IFN-γ and the gene coding for IL-12 carried out on D9 post-immunostimulation are shown in FIGS. 8-A and 8-B respectively. The mouse pups in the control batch (A) have not developed an inflammatory response (secretion of IL-12 and IFN-γ) on D9 post-infection. In contrast, 9 days after immunostimulation, the mouse pups No. 4, 5 and 6 display significantly greater expression of IL-12 than that of the mouse pups in the control batches (FIG. 8-B). Similarly, two mouse pups out of 3 in the batch immunostimulated with the strain Toxo mic1-3 KO display expression of IFN-γ significantly greater than that of the mouse pups in the control batches (FIG. 8-A); these are the mouse pups No. 4 and No. 6.

2.3—Investigation of the State of Infection of the Mouse Pups 2.3.1—Dissemination of the Spleens on HFF Cells The dissemination of the spleens on HFF cells is illustrated in Table IX. No lysis plaque is detected in the HFF cells infected with the spleens from the mouse pups of the control batch. In contrast, the HFF cells infected with the ground material from the spleen originating from the mouse pups immunostimulated with the strain Toxo mic1-3 KO have lysis plaques, demonstrating that tachyzoites are present in the spleen.

Moreover, the technique of tissue dissemination of the tachyzoites on HFF cells is a semiquantitative technique which shows that the mouse pups in the batch immunostimulated with the strain Toxo mic1-3 KO have different states of infection. The mouse pups No. 4 and No. 6 seem be the most infected as they have the largest number of parasites in the spleen, followed by mouse pup No. 5, which has far fewer parasites in the spleen (Table IX).

TABLE IX

Result of optical microscopy analysis, of the dissemination of the organs on human fibroblast cells (HFF). The tachyzoites observed originate from the spleens of the mouse pups immunostimulated with the strain Toxo mic1-3 KO and form lysis plaques when they colonize the HFF cells.

| | Presence of parasites | Lysis plaques observed |
|---|---|---|
| Control mouse pup 4 | NO | 0 |
| Control mouse pup 5 | NO | 0 |
| Control mouse pup 6 | NO | 0 |
| Immunostimulated mouse pup 4 | YES | >70% of the lysed cells |
| Immunostimulated mouse pup 5 | YES | 2 |
| Immunostimulated mouse pup 6 | YES | >70% of the lysed cells |

2.3.2—Immunohistology

The immunohistology sections of the intestines from the mouse pups are illustrated in FIG. 9.

For the mouse pups in the control batch, no tachyzoite was observed on the immunohistology sections.

The sections of intestine from the mouse pups No. 4 (B) and No. 6 (D) and No. 5 respectively (data not shown), immunolabelled with a rabbit anti-*T. gondii* polyclonal antibody, allow visualization of the presence of tachyzoites of the strain Toxo mic1-3 KO (white dots) for the mouse pup No. 4 only.

2.3.3—PCR

The PCR results are presented in FIG. 10. Amplification of the SAG1 gene of *Toxoplasma gondii* from a DNA sample originating from ground material from the ileum is representative of the presence of Toxo mic1-3 KO tachyzoites (amplified fragment at 1001 bp). This semiquantitative technique shows absence of a band for the mouse pups in the control batch (NV) sacrificed on D3 (T1) or on D9 (T2).

For the mouse pups immunostimulated with the strain Toxo mic1-3 KO (V), no band corresponding to the SAG1 gene is detected 3 days after infection. On D9, two mouse pups out of 3 display a band of DNA of 1001 base pairs, providing evidence of the presence of Toxo mic1-3 KO tachyzoites. The intensity of the bands observed between the mouse pups No. 4 and No. 6 is clearly different. As the intensity of the bands is proportional to the number of parasites present in the intestine, the mouse pup No. 4 has more parasites in the intestine than the mouse pup No. 6, 9 days post-infection. These results confirm the observation made by immunohistology.

Example 5

Protection Against Cryptosporidiosis of the Mouse Pups Immunostimulated with the Mutant Toxo mic1-3 KO by Intraperitoneal Route 1—Experimental Protocol
1.1—Animals Immunostimulation is carried out on C57BL/6 mouse pups aged 3 days. These mouse pups were obtained and bred in the INRA Centre in Nouzilly (Indre et Loire). The mouse pups are kept throughout the experiments in an animal house of containment level 2 in order to limit the risk of external contamination as far as possible.

1.2—*Cryptosporidium parvum*

The oocysts of *Cryptosporidium parvum* are obtained from excrement of calves infected with $10^7$ *C. parvum* oocysts. The stool undergoes various treatments until a suspension of purified, sterile parasites is obtained, suitable for use in cell culture. Throughout the treatment, the oocysts are manipulated at 4° C., to prevent excystation of the oocysts.

Briefly, after recovery of the stool, the latter is diluted in fresh water and then passed through a 100-µm filter and centrifuged at 1900 g for 10 minutes at 4° C. The pellets obtained, containing the oocysts, are taken up in 2% potassium dichromate solution (Prolabo, ref. 26 776 290, CAS 7778-50-9), then washed twice with cold water by centrifugation at 1900 g for 10 minutes at 4° C. to remove the potassium dichromate. After washing, the pellet of coccidia is taken up in a mixture of water and ether (Ethyl Ether, Carlo Erba, CAS No. 60-29-7) diluted to 1/5, and then is centrifuged again at 1900 g for 10 minutes at 4° C. The upper phases containing the fats and the ether are removed and the pellet is recovered and taken up in cold water after passing through a 20-µm filter. Two to three millilitres of the suspension of parasites obtained is deposited on a glucose gradient prepared from Sheather solution (sucrose 500 g, water 320 ml, 0.2 g of sodium azide (Prolabo, CAS 26628-22-8)). Two rings of oocysts are formed after centrifugation of the glucose gradient at 2000 g for 20 minutes at 4° C. The two rings are recovered and washed several times in cold water. The purified oocysts are then sterilized. After centrifugation at 1900 g for 10 minutes at 4° C., the pellet of oocysts is incubated for 15 minutes in a solution of bleach (sodium hypochlorite (Sigma 239305-500ML Titre: 4.5% of active chlorine) diluted to 10% in demineralized water, then washed 3 times in sterile 1×PBS (diluted from a solution of 10×PBS: sodium chloride, NaCl 80 g/litre water; potassium chloride, KCl 2 g/litre; potassium dihydrogen phosphate, $KH_2PO_4$: 2 g/litre; disodium hydrogen phosphate, $Na_2HPO_4$, 12 $H_2O$: 29 g/litre). The purified and sterilized oocysts are counted on a slide (5 µL of solution of oocysts and 495 µL of malachite green), adjusted to a concentration of $2\times10^8$ oocysts/mL, divided into aliquots in 1.5-mL tubes and stored at 4° C.

1.3—Strain Toxo mic1-3 KO

The mutant strain of *Toxoplasma gondii*, in which the genes coding for the proteins MIC1 and MIC3 have been knocked out (called strain Toxo mic1-3 KO) is maintained by successive passages on a human foreskin fibroblast (HFF) line cultured in DMEM medium supplemented with 10% of foetal calf serum (FCS), 2 mM of glutamine, 50 U/mL of penicillin and 50 µg/mL of streptomycin.

1.4—Immunostimulation

Batches of C57BL/6 mouse pups aged 3 days were treated as follows:
7 mouse pups (batch 1) received the mutant Toxo mic1-3 KO
7 mouse pups (batch 2) served as unvaccinated control batch.

On D0, the mouse pups in batch 1 received 20 tachyzoites of the strain Toxo mic1-3 KO by intraperitoneal route.

On D3 post-immunostimulation, the mouse pups in batch 1 and batch 2 were challenged with 500,000 parasites of *Cryptosporidium parvum*.

On D9 post-infection, the mouse pups in batch 1 and 2 were sacrificed in order to evaluate protection against *Cryptosporidium parvum*.

1.5—Investigation of the State of Infection of the Mouse Pups

The state of infection of the mouse pups was analysed by the technique of tissue dissemination of the tachyzoites on HFF cells described above. The HFF cells are deposited in a 24-well plate, one week before depositing the organs at a rate of $10^4$ cells per well. The cells are cultured in 1 mL of DMEM cell culture medium supplemented with 10% of foetal calf serum (FCS), 2 mM of glutamine, 50 U/mL of penicillin and 50 µg/mL of streptomycin. After sacrifice of the mouse pups, the spleen of each of the mouse pups is taken and ground in 2 mL of 1×PBS. Ten microlitres of ground material is deposited per well containing the HFF cells cultured in 1 mL of medium. Twenty-four hours after depositing the ground material from the spleen, the cells are washed in DMEM and then 1 mL of clean medium is deposited per well. The cells are cultured until the lysis plaques revealing the presence of Toxo mic1-3 KO tachyzoites are detected.

1.6—Investigation of Protection

The protection of the mouse pups against *Cryptosporidium parvum* is analysed by counting the oocysts in the intestine. After the mouse pups are sacrificed, the intestines are recovered, weighed, placed in 1 mL of water (4° C.) and ground for 20 seconds. 100 microlitres of ground material is added to 400 µL of sugar solution at 4° C. (500 g of powdered sugar, 320 mL of distilled water, Na azide at 0.02%). After homogenizing the solution by pipetting, 20 µL is deposited on a Thoma cell. Before counting the oocysts, the slides are kept in a cool place for 15 minutes to allow the oocysts in the sugar solution to rise to the surface. The total number of oocysts in the intestine is calculated by means of the following formula: Total number of oocysts of *C. parvum* in the intestine=Number of oocysts counted on Thoma slide×dilution factor×10 000×(1+weight of the mouse pup intestine).

2—Results 2.1—Investigation of the State of Infection of the Mouse Pups

The state of infection of the mouse pups is evaluated from parasitaemia in the case of *Cryptosporidium parvum* (*C. parvum*) and *Toxoplasma gondii* (*T. gondii*). Parasitaemia in the case of *C. parvum* is determined by the total number of oocysts of *C. parvum* counted in the mouse pup intestine. Parasitaemia in the case of *T. gondii* is evaluated by dissemination of the spleens of the mouse pups on HFF cells. The parasitaemias for *C. parvum* and *T. gondii* are presented in Table X.

TABLE X

Summary table of parasitaemia observed in the case of *C. parvum* and in the case of *T. gondii* of the batch of the mouse pups infected with *C. parvum* (infected *C. parvum*) and of the batch of the mouse pups inoculated with *T. gondii* and infected with *C. parvum* (inoculated *T. gondii* + *C. parvum*): t, tachyzoites; NR, data not reported. The number associated with parasitaemia in the case of *T. gondii* corresponds to the number of tachyzoites counted in 20 μL of supernatant of the HFF cells infected after dissemination of the spleen.

| Infected *C. parvum* | | | Inoculated *T. gondii* + *C. parvum* | | |
|---|---|---|---|---|---|
| mouse pups | Total number of oocysts of *C. parvum* | Parasit-aemia *T. gondii* | mouse pups | Total number of oocysts of *C. parvum* | Parasit-aemia *T. gondii* |
| 1 | 862500 | NO | 1 | 935000 | SLIGHT (6.6 $10^5$ t.) |
| 2 | 966500 | NO | 2 | 53000 | YES (NR) |
| 3 | 1083000 | NO | 3 | 55000 | YES (2 $10^6$ t.) |
| 4 | 565000 | NO | 4 | 1568000 | VERY SLIGHT (2 $10^5$ t.) |
| 5 | 684000 | NO | 5 | 832500 | VERY SLIGHT (1.2 $10^5$ t.) |
| 6 | 847500 | NO | 6 | 754000 | VERY SLIGHT (1.6 $10^5$ t.) |
| 7 | 994500 | NO | 7 | 330000 | YES (1.24 $10^6$ t.) |

The mouse pups infected with *C. parvum* only, have a total number of oocysts of *C. parvum* in the intestine in the range from $5 \times 10^5$ to $1 \times 10^6$ oocysts.

The mouse pups immunostimulated with the strain Toxo mic1-3 KO and then infected with *C. parvum* display *T. gondii* parasitaemia varying from one mouse pup to another. For mouse pups No. 2, 3 and 7, which have the highest *T. gondii* parasitaemia, the total number of oocysts of *C. parvum* in the intestine varies from $5 \times 10^4$ to $3.3 \times 10^5$ oocysts. These results demonstrate the correlation that exists between parasitaemia with Toxo mic1-3 KO and the reduction in *C. parvum* infection.

2.2—Investigation of Protection

The state of protection of the mouse pups is shown in FIG. 11.

In the batch of the mouse pups vaccinated by intraperitoneal route with the mutant Toxo mic1-3 KO, 3 mouse pups out of 7 have a total number of oocysts of *C. parvum* in the intestine that is significantly reduced, by approximately 62% to 94%. These three mouse pups are the mouse pups No. 2, No. 3 and No. 7, which displayed the highest parasitaemia with *T. gondii* of all the mouse pups in this group.

Example 6

Protection Against Cryptosporidiosis, of the Mouse Pups Immunostimulated with the Mutant Toxo Mic1-3 KO by Oral Route 1—Experimental Protocol 1.1—Animals Immunostimulation is carried out on C57BL/6 mouse pups aged 3 days. These mouse pups were obtained and bred in the INRA Centre in Nouzilly (Indre et Loire). The mouse pups are kept throughout the experiments in an animal house of containment level 2 in order to limit the risk of external contamination as far as possible.

1.2—*Cryptosporidium parvum*

Oocysts of *Cryptosporidium parvum* are obtained from excrement of calves infected with $10^7$ *C. parvum* oocysts. The stool undergoes various treatments until a suspension of sterile, purified parasites is obtained, suitable for use in cell culture. Throughout the treatment, the oocysts are manipulated at 4° C. to prevent excystation of the oocysts.

Briefly, after recovery of the stool, the latter is diluted in fresh water and then passed through a 100-nm filter and centrifuged at 1900 g for 10 minutes at 4° C. The pellets obtained, containing the oocysts, are taken up in 2% potassium dichromate solution (Prolabo ref. 26 776 290, CAS 7778-50-9), then washed twice with cold water by centrifugation at 1900 g for 10 minutes at 4° C. to remove the potassium dichromate. After washing, the pellet of coccidia is taken up in a mixture of water and ether (ethyl ether, Carlo Erba CAS No. 60-29-7) diluted to 1/5, then centrifuged again at 1900 g for 10 minutes at 4° C. The upper phases containing the fats and the ether are removed and the pellet is recovered and taken up in cold water after passing through a 20-μm filter. Two to three millilitres of the suspension of parasites obtained is deposited on a glucose gradient prepared from Sheather solution (sucrose 500 g, water 320 ml, 0.2 g of sodium azide (Prolabo, CAS 26628-22-8)). Two rings of oocysts are formed after centrifugation of the glucose gradient at 2000 g for 20 minutes at 4° C. The two rings are recovered and washed several times in cold water. The purified oocysts are then sterilized. After centrifugation at 1900 g for 10 minutes at 4° C., the pellet of oocysts is incubated for 15 minutes in a solution of bleach (sodium hypochlorite, Sigma 239305-500ML Titre: 4.5% of active chlorine) diluted to 10% in demineralized water and then washed 3 times in sterile 1×PBS (diluted from a solution of 10×PBS: sodium chloride, NaCl 80 g/litre water; potassium chloride, KCl 2 g/litre; potassium dihydrogen phosphate, $KH_2PO_4$: 2 g/litre; disodium hydrogen phosphate, $Na_2HPO_4$, 12 $H_2O$: 29 g/litre). The purified and sterilized oocysts are counted on a slide (5 μL of solution of oocysts and 495 μL of malachite green), adjusted to a concentration of $2 \times 10^8$ oocysts/mL, divided into aliquots in 1.5-mL tubes and stored at 4° C.

1.3—Strain Toxo mic1-3 KO

The mutant strain of *Toxoplasma gondii*, in which the genes coding for the proteins MIC1 and MIC3 have been suppressed (called strain Toxo mic1-3 KO) is maintained by successive passages on a human foreskin fibroblast (HFF) line cultured in DMEM medium supplemented with 10% of foetal calf serum (FCS), 2 mM of glutamine, 50 U/mL of penicillin and 50 μg/mL of streptomycin.

1.4—Immunostimulation

Batches of C57BL6 mouse pups aged 3 days were treated as follows:

4 mouse pups (batch 1) received the mutant Toxo mic1-3 KO 4 mouse pups (batch 2) served as untreated control batch. On D0, the mouse pups in batch 1 received 20,000 tachyzoites of the strain Toxo mic1-3 KO by oral route.

On D3 post-immunostimulation, the mouse pups in batch 1 and batch 2 were challenged with 1,000,000 parasites of *Cryptosporidium parvum*, On D10 post-immunostimulation, the mouse pups in batch 1 and 2 were sacrificed to evaluate protection against *Cryptosporidium parvum*.

1.5—Investigation of the State of Infection of the Mouse Pups

The state of infection of the mouse pups was analysed by the technique of tissue dissemination of the tachyzoites on HFF cells described above. The HFF cells are deposited in a 24-well plate, one week before depositing the organs at a rate of $10^4$ cells per well. The cells are cultured in 1 mL of DMEM cell culture medium supplemented with 10% of foetal calf serum (FCS), 2 mM of glutamine, 50 U/mL of penicillin and 50 µg/mL of streptomycin. After sacrifice of the mouse pups, the spleen of each of the mouse pups is taken and ground in 2 mL of 1×PBS. Ten microlitres of ground material is deposited per well containing the HFF cells cultured in 1 mL of medium. Twenty-four hours after depositing the ground material from the spleen, the cells are washed in DMEM and then 1 mL of clean medium is deposited per well. The cells are cultured until the lysis plaques revealing the presence of Toxo mic1-3 KO tachyzoites are detected.

1.6—Investigation of Protection

The protection of the mouse pups against *Cryptosporidium parvum* is analysed by counting the oocysts in the intestine. Once the mouse pups have been sacrificed, the intestines are recovered, weighed, placed in 1 mL of water (4° C.) and ground for 20 seconds. 100 microlitres of ground material is added to 400 µl of sugar solution at 4° C. (500 g of sucrose, 320 mL of distilled water, Na azide at 0.02%). After homogenizing the solution by pipetting, 20 µL is deposited on a Thoma slide. Before counting the oocysts, the slides are kept in a cool place for 15 minutes to allow the oocysts in the sugar solution to rise to the surface. The total number of oocysts in the intestine is calculated from the following formula: Total number of oocysts of *C. parvum* in the intestine=Number of oocysts counted on Thoma slide× dilution factor×10,000×(1+weight of the intestine of the mouse pup).

2—Results 2.1—Investigation of the State of Infection of the Mouse Pups Dissemination of the Spleens on HFF Cells Dissemination of the spleens on HFF cells is illustrated in Table XI.

TABLE XI

Summary table of parasitaemia observed in the case of *C. parvum* and in the case of *T. gondii* of the batch of the mouse pups infected with *C. parvum* (infected *C. parvum*) and of the batch of the mouse pups inoculated with Toxo mic1-3 KO and infected with *C. parvum* (inoculated *T. gondii* + *C. parvum*).

| | Inoculated *C. parvum* | | | Inoculated *T. gondii* + *C. parvum* | |
|---|---|---|---|---|---|
| mouse pups | Total number of oocysts of *C. parvum* | Parasitaemia *T. gondii* | mouse pups | Total number of oocysts of *C. parvum* | Parasitaemia *T. gondii* |
| 1 | 2240000 | NO | 1 | 260000 | YES |
| 2 | 1794000 | NO | 2 | 476000 | YES |
| 3 | 1370000 | NO | 3 | 2046000 | SLIGHT |
| 4 | 2448000 | NO | 4 | 1687500 | SLIGHT |

The mouse pups infected only with *C. parvum* have a total number of oocysts of *C. parvum* in the intestine in the range from $1.4 \times 10^6$ to $2.4 \times 10^6$ oocysts.

The mouse pups immunostimulated with Toxo mic1-3 KO and then infected with *C. parvum* display *T. gondii* parasitaemia determined semiquantitatively. For the mouse pups No. 1 and 2, which have severe *T. gondii* parasitaemia, the total number of oocysts of *C. parvum* in the intestine varies from $2.6 \times 10^5$ to $4.8 \times 10^5$ oocysts. These results demonstrate the correlation that exists between parasitaemia with *T. gondii* mic1-3 KO and the reduction in infection with *C. parvum*.

2.2—Investigation of Protection

The state of protection of the mouse pups is shown in FIG. 12.

In the batch of the mouse pups vaccinated with the mutant Toxo mic1-3 KO by oral route, two mouse pups out of 4 have a total number of oocysts of *C. parvum* in the intestine that is significantly reduced by approximately 75% and 87%. These are the mouse pups No. 1 and No. 2.

Example 7

Induction of Secretion of IL-12 and of IFN-γ of Splenocytes and Induction of Secretion of IL-12 of MLN Cells Originating from Adult or Neonate Sheep after Stimulation with the Mutant Toxo mic1-3 KO 1—Experimental Protocol 1.1—Animals The mesenteric lymph nodes and the spleens of neonates used in this experiment originate from lambs of the Ile de France breed aged 6-12 days. Until sacrifice, the lambs were kept with their mothers in a sealed mouse house (INRA—Nouzilly) in order to limit the risks of natural contamination. They were anaesthetized by electronarcosis and then euthanased to collect the different organs. Only the animal keepers and the experimenters, equipped with clothing for use inside the sheep house, may enter the buildings, in order to avoid contamination of the environment, and they only leave the sealed zone after showering. The utensils used and the biological material are only taken out after passing through a disinfectant bath, and the waste is incinerated.

The mesenteric lymph nodes and the spleens of adult subjects used in this experiment originate from adult sheep of the Ile de France breed aged from 1 to 3 years.

1.2—Strains of *Toxoplasma gondii*

The wild-type RH and Pru strains and the mutant strain Toxo mic1-3 KO are maintained by successive passages on a human foreskin fibroblast (HFF) line cultured in DMEM medium supplemented with 10% of foetal calf serum (FCS), 2 mM of glutamine, 50 U/mL of penicillin and 50 µg/mL of streptomycin.

1.3—Isolation of the Cells of Interest 1.3.1—Cells of the Mesenteric Lymph Nodes The mesenteric lymph nodes are removed as quickly as possible after the animals are euthanased, and transferred to a sterile sample tube containing culture medium (HBSS supplemented with 2% foetal calf serum (FCS) and 1% penicillin/streptomycin (P/S)). The sample tube containing the sample is stored in ice until it reaches the research laboratory.

Each lymph node is defatted using previously sterilized forceps, scissors or scalpel. The lymph node is then deposited on a sterile (autoclaved) nylon mesh measuring 3 cm×3 cm placed at the bottom of a sterile Petri dish containing 10 mL of medium (HBSS; 2% FCS; 1% P/S). The lymph node is crushed and comminuted using a piston of a 5-mL syringe to release the cells contained in the lymph node. The medium thus enriched with cells is filtered using a 60-µm sterile nylon cloth positioned above a 50-mL tube for recovering the medium enriched with filtered cells. These last steps are repeated twice as follows: 10 mL of medium is added to the remaining fragments of lymph nodes. The fragments of lymph nodes are crushed, comminuted and filtered as described above. The 50-mL tube for recovering the filtered cell-enriched medium is centrifuged at 1600 g for 15 min at 4° C. Washing is carried out with 50 mL of medium (HBSS; 2% FCS; 1% P/S) by centrifugation for 10 min at 400 g at 4° C. The pellet thus obtained is resuspended in a final volume of 90 mL of medium (HBSS; 2% FCS; 1% P/S) at ambient temperature in two 50-mL tubes.

The 90 mL of cell suspension is divided into 3 to be purified in a Ficoll-Hypaque gradient. 30 mL is carefully deposited per tube (3 tubes in total) containing 15 mL of Ficoll-Hypaque. The 3 tubes of Ficoll-Hypaque enriched with cell suspension are centrifuged at 1500 g without braking (deceleration 2, acceleration 5), for 30 minutes at room temperature. For each tube of Ficoll-Hypaque, an upper phase is obtained composed of cell debris, a ring composed of mononuclear cells, positioned as an interphase between the cell debris and the Ficoll phase, and finally a lower phase composed of red blood cells. The 3 rings (20 mL/tubes) are recovered and divided into two 50-mL tubes and washed with a final volume of 50 mL of medium (HBSS; 2% FCS; 1% P/S) at 700 g for 10 min. The pellets of mononuclear cells obtained are pooled. The final pellet is washed with 50 mL of medium (HBSS; 2% FCS; 1% P/S) by centrifugation at 400 g for 10 min. The pellet is taken up in 5 mL of RPMI, 10% FCS, 1% P/S, $5.10^{-5}$M of beta-mercaptoethanol. The mononuclear cells are stored in ice; a proportion of the cells is used for counting and observation of viability with Trypan blue (sample diluted to 1/100). Once counted, the cells are distributed in a 96-well plate at a rate of $3.10^5$ cells/well.

1.3.2—Isolation of the Splenocytes

The spleen is removed as quickly as possible after euthanasia and transferred to a sterile sample tube containing culture medium (HBSS; 2% FCS; 1% P/S). The sample tube containing the sample is stored in ice until it reaches the research laboratory.

Each spleen is defatted using previously sterilized forceps, scissors or scalpel. The spleen is then deposited on a metal grid (autoclaved) placed at the bottom of a sterile Petri dish containing 10 mL of medium (HBSS; 2% FCS; 1% P/S). The spleen is crushed and comminuted using a piston of a 5-mL syringe to release the cells contained in the spleen. The medium thus enriched with cells is deposited in a 50-mL tube. These last steps are repeated twice as follows: 5 mL of medium is added to the fragments of spleen. The fragments of spleen are crushed and comminuted as described above. The 50-mL tube for recovery of the medium enriched with cells is left to settle for 5 min at 4° C. The supernatant is filtered on a 60 μm nylon mesh above a 50-mL tube. Ten millilitres of medium is added to the remaining sediments and the second supernatant is recovered in the same way. The 50-mL tube for recovery of the two supernatants is centrifuged for 30 s at 400 g at 4° C. The supernatant is recovered and filtered on a 60-μm sterile nylon mesh above a 50-mL tube. This last tube is centrifuged for 10 min at 400 g at 4° C. The cell pellet thus obtained is resuspended in a final volume of 50 mL of medium (HBSS; 2% FCS; 1% P/S). Washing is carried out by centrifugation for 10 min at 400 g at 4° C. The pellet is then taken up in a final volume of 120 mL in three 50-mL tubes of medium (HBSS; 2% FCS; 1% P/S) at room temperature.

The 120 mL of cell suspension is divided into 3 to be purified in a Ficoll-Hypaque gradient. 30 mL is carefully deposited per tube (4 tubes in total) containing 15 mL of Ficoll-Hypaque. The 4 tubes of Ficoll-Hypaque enriched with cell suspension are centrifuged at 1500 g without braking (deceleration 2, acceleration 5), for 30 minutes at room temperature. For each tube of Ficoll-Hypaque, an upper phase is obtained composed of cell debris, a ring composed of mononuclear cells positioned as an interphase between the cell debris and the Ficoll phase, and finally a lower phase composed of red blood cells. The 4 rings (20 mL/tubes) are recovered and divided into three 50-mL tubes and washed with a final volume of 50 mL of medium (HBSS; 2% FCS; 1% P/S) at 700 g for 10 min. The pellets of mononuclear cells obtained are pooled. The final pellet is washed with 50 mL of medium (HBSS; 2% FCS; 1% P/S) by centrifugation at 400 g for 10 min. The pellet is taken up in 5 mL of RPMI, 10% FCS, 1% P/S, $5.10^{-5}$M of beta-mercaptoethanol. The mononuclear cells are stored in ice; a proportion of the cells is used for counting and observation of viability with trypan blue (sample diluted to 1/100). Once counted, the cells are distributed in a 96-well plate at a rate of $3.10^5$ cells/well.

1.4—Stimulation of the Mononuclear Cells of the Lamb Mesenteric Lymph Nodes and Splenocytes Once counted, the cells are distributed in a 96-well plate at a rate of $3.10^5$ cells/well. The tachyzoites are also counted on a Malassey slide; pellets are obtained and are taken up in RPMI medium, 10% FCS, 1% P/S. The solutions of the tachyzoites (RH or KO) are adjusted to obtain a concentration of $3.10^6$ tachyzoites/mL. The conditions for stimulation are as follows: 3 mononuclear cells are stimulated per tachyzoite. Parasites, lymph node mononuclear cells and spleen mononuclear cells are cultured at 37° C. in a stove at 5% $CO_2$ and 95% humidity.

24 h post-stimulation, the supernatants of the lymph node mononuclear cells and the supernatants of the spleen mononuclear cells are used for assay of interleukin-12 and IFN-γ by the ELISA technique.

1.5—Assay of Interleukin-12 by the ELISA Technique

The technique used for assay of interleukin-12 is an ELISA of the sandwich type on a 96-well plate. The antibody (anti-IL-12) immobilized on a plate reacts specifically with the IL-12 present in the test sample. The quantity of antigen-antibody is measured for a second time after it has reacted with an antibody of identical specificity coupled to an enzyme.

All the dilutions of the different reagents are carried out with 1×PBS, 0.05% Tween 20 and 1% BSA except for the capture antibody, which is diluted in 1×PBS.

50 μL per well of capture antibodies diluted to 1/500 (Mouse anti-bovine interleukin-12 clone CC 301, Serotec MCA1782EL, Initial concentration: 1000 μg/mL) is deposited in an ELISA plate (ELISA plate Nunc maxisorp 442404) and then incubated overnight at 4° C. Three washings are carried out in 1×PBS buffer with the addition of 0.05% Tween 20 (PBS-T). The non-specific sites are saturated by incubating the plates for 1 hour at room temperature with 200 μL of a 1×PBS solution; 0.05% Tween 20, 1% BSA. Three washings are carried out in 1×PBS buffer with the addition of 0.05% Tween 20 (PBS-T).

The range is prepared as follows: 50 μL of the standard range of rov IL-12 is deposited at different concentrations: 16 U/mL, 8 U/mL, 4 U/mL, 2 U/mL, 1 U/mL, 0.5 U/mL, 0.25 U/mL, 0.125 U/mL, 0.0625 U/mL, 0.03125 U/mL. In parallel, the samples (supernatant of stimulated mononuclear cells, diluted 1/2) are deposited at a rate of 50 μL per well. The samples and the standard range are incubated for 1 h at room temperature. 4 washings are carried out in 1×PBS buffer with the addition of 0.05% Tween 20 (PBS-T).

50 μL of biotinylated detection antibodies (Mouse anti-bovine interleukin-12: biotin clone CC 326 (Serotec MCA2173B) Initial concentration: 500 μg/ml) diluted to 1/500 is deposited per well, for an incubation time of one hour at room temperature. A series of 4 washings is carried out in 1×PBS buffer with the addition of 0.05% Tween 20 (PBS-T).

IL-12 is detected by a biotin-ExtrAvidine® affinity reaction followed by a colorimetric reaction between peroxidase and its substrate: 50 µL of modified avidin coupled to a peroxidase (ExtrAvidine-Peroxidase Conjugate® (Sigma E2886)) diluted to 1/2000th is deposited per well and incubated for 20 minutes at room temperature. A series of 4 washings is carried out in 1×PBS buffer with the addition of 0.05% Tween 20 (PBS-T). Detection is carried out using 50 µL/well of peroxidase substrate originating from a solution A and B mixed volume for volume (TMB Peroxidase substrate Eurobio KPL solution A 50-76-01 and solution B 50-65-00). The substrate solution is incubated for 15 minutes at room temperature. 50 µL of stopping solution (phosphoric acid 1M Sigma 43,080-1, CAS 7664-38-2) is added per well under a fume hood.

The plates are read at wavelength λ=450 nm. The standard curve is determined by the following function: OD value as a function of the concentration of recombinant IL-12. The OD values of the samples tested are converted to concentration using the standard curve. To be taken into account, the samples must give ODs located on the linear portion of the standard curve.

1.6—Assay of Interferon Gamma by the ELISA Technique

The technique used for assay of interferon is an ELISA, comparable to the assay of interleukin-12 described in the preceding paragraph, of the sandwich type on a 96-well plate. The antibody (anti-IFNγ) immobilized on a plate reacts specifically with the IFNγ present in the test sample. The quantity of antigen-antibody is measured for a second time after it has reacted with an antibody of identical specificity to an enzyme.

All the dilutions of the different reagents are prepared in 1×PBS, 0.05% Tween 20 and 1% BSA except for the capture antibody, which is diluted in 1×PBS.

50 µl per well of capture antibodies diluted to 1/500 (Mouse anti-bovine interferon gamma clone CC 330, Serotec MCA2112, Initial concentration: 1000 µg/mL) is deposited in an ELISA plate (ELISA plate Nunc maxisorp 442404) and then incubated overnight at 4° C. Three washings are carried out in 1×PBS buffer with the addition of 0.05% Tween 20 (PBS-T). The non-specific sites are saturated by incubating the plates for 1 hour at room temperature with 200 µL of a solution 1×PBS; 0.05% Tween 20, 1% BSA. Three washings are carried out in 1×PBS buffer with the addition of 0.05% Tween 20 (PBS-T).

The range is prepared as follows: 50 µL of the standard range of Recombinant bovine IFNγ (Perbio Endogen robIFNGγ, initial concentration: 30 µg/ml) is deposited at different concentrations: 4 ng/mL, 2 ng/mL, 1 ng/mL, 0.5 ng/mL, 0.25 ng/mL, 0.125 ng/mL, 0.0625 ng/mL, 0.03125 ng/mL, 0.015 ng/ml). In parallel, the samples (supernatant of stimulated mononuclear cells, diluted 1/2) are deposited at a rate of 50 µL per well. The samples and the standard range are incubated for 1 h at room temperature. 4 washings are carried out in 1×PBS buffer with the addition of 0.05% Tween 20 (PBS-T).

50 µL of biotinylated detection antibodies (Mouse anti-bovine interferon gamma: biotin clone CC 302 (Serotec MCA1783B) Initial concentration: 500 µg/ml) diluted to 1/500 is deposited per well, for an incubation time of one hour at room temperature. A series of 4 washings is carried out in 1×PBS buffer with the addition of 0.05% Tween 20 (PBS-T).

IFNγ is detected by a biotin-ExtrAvidine® affinity reaction followed by a colorimetric reaction between peroxidase and its substrate: 50 µL of modified avidin coupled to a peroxidase (ExtrAvidine-Peroxidase Conjugate® (Sigma E2886)) diluted to 1/2000th is deposited per well and incubated for 20 minutes at room temperature. A series of 4 washings is carried out in 1×PBS buffer with the addition of 0.05% Tween 20 (PBS-T). Detection is carried out using 50 µL, per well of peroxidase substrate originating from a solution A and B mixed volume for volume (TMB Peroxidase substrate Eurobio KPL solution A 50-76-01 and solution B 50-65-00). The substrate solution is incubated for 15 minutes at room temperature. 50 µL of stopping solution (phosphoric acid 1M Sigma 43,080-1, CAS 7664-38-2) is added per well under a fume hood.

The plates are read at wavelength λ=450 nm. The standard curve is determined by the following function: OD value as a function of the concentration of recombinant IFNγ. The OD values of the samples tested are converted to concentration using the standard curve. To be taken into account, the samples must give ODs located on the linear portion of the standard curve.

2—Results

The level of IL-12 and of IFN-γ secreted by the mononuclear cells of spleens and the level of IL-12 secreted by the mononuclear cells of mesenteric lymph nodes (MLN) isolated from lambs aged from 6 to 12 days and from adult sheep aged from 1 to 3 years and stimulated with different strains of the parasite *Toxoplasma gondii* are shown in FIGS. 13-A, 13-B and 13-C.

In the sheep aged from 1 to 3 years, production of IL-12 by the mononuclear cells originating from the spleen or from the mesenteric lymph nodes is greater when the latter have been stimulated in vitro by the mutant strain Toxo mic1-3 KO or by the wild-type Pru and RH strains of *T. gondii*. This observation is more pronounced in the case of cells from the mesenteric lymph nodes of adult sheep.

In the lambs aged from 6 to 12 days, production of IL-12 by the mononuclear cells originating from the spleen or from the mesenteric lymph nodes is greater when the latter have been stimulated in vitro by the parasite *T. gondii*. Production of IL-12 is even greater when the mononuclear cells have been stimulated in vitro by the mutant strain Toxo mic1-3 KO.

In the sheep aged from 1 to 3 years, production of IFNγ by the mononuclear cells originating from the spleen does not differ significantly when the latter have been stimulated in vitro by the mutant strain mic1-3 KO or by the wild-type strains Pru and RH of *T. gondii*.

In the lambs aged from 6 to 12 days, production of IFNγ by the mononuclear cells originating from the spleen does not differ significantly when the latter have been stimulated in vitro by the mutant strain mic1-3 KO or by the wild-type strains Pru and RH of *T. gondii*.

Production of IL-12 and IFN-γ by the mononuclear cells originating from lambs is much greater than that observed for the mononuclear cells from the adult sheep.

Example 8

Immunostimulation of Neonate Lambs by the Mutant *Toxoplasma gondii* Toxo *mic*1-3 KO 1—Experimental Protocol 1.1—Animals Immunostimulation is carried out on 1-day-old neonate lambs. After ingestion of colostrum, the lambs were isolated from their mothers in a sealed sheep house (INRA—Nouzilly) in order to limit the risks of natural contamination. They were anaesthetized by electronarcosis and then euthanased to collect the various organs. Only the animal keepers and the experimenters, equipped with clothing for use inside the animal house, may enter the buildings, to prevent contamination of the environment, and they only leave the sealed zone after showering.

1.2—Strain Toxo mic1-3 KO

The mutant strain of *Toxoplasma gondii*, in which the genes coding for the proteins MIC1 and MIC3 have been suppressed (called strain Toxo mic1-3 KO) is maintained by successive passages on a human foreskin fibroblast (HFF) line cultured in DMEM medium supplemented with 10% of foetal calf serum (FCS), 2 mM of glutamine, 50 U/mL of penicillin and 50 µg/mL of streptomycin.

1.3—Immunostimulation

Six one-day-old lambs were treated as follows:
4 lambs (batch A) received the mutant Toxo mic1-3 KO
2 lambs (batch B) served as unvaccinated control batch.

On D1, the lambs in batch A received $10^6$ tachyzoites of the strain Toxo mic1-3 KO subcutaneously. After immunostimulation, the temperatures and the weights of the lambs are recorded daily.

On D15 post-immunostimulation, the lambs are euthanased for investigating the immune response and parasitaemia.

1.4—Isolation of the Cells of Interest 1.4.1—Isolation of the Splenocytes

The spleen is removed as quickly as possible after euthanasia and transferred to a sterile sample tube containing culture medium (HBSS; 2% FCS; 1% P/S). The sample tube containing the sample is stored in ice until it reaches the research laboratory.

Each spleen is defatted using previously sterilized forceps, scissors or scalpel. The spleen is then deposited on a metal grid (autoclaved) placed at the bottom of a sterile Petri dish containing 10 mL of medium (HBSS; 2% FCS; 1% P/S). The spleen is crushed and comminuted using a piston of a 5-mL syringe to release the cells contained in the spleen. The medium thus enriched with cells is deposited in a 50-mL tube. These last steps are repeated twice as follows: 5 mL of medium is added to the fragments of spleen. The fragments of spleen are crushed and comminuted as described above. The 50-mL tube for recovery of the cell-enriched medium is left to settle for 5 min at 4° C. The supernatant is filtered on a 60 µm nylon mesh above a 50-mL tube. Ten millilitres of medium is added to the remaining sediments and the second supernatant is recovered in the same way. The 50-mL tube for recovery of the two supernatants is centrifuged for 30 s at 400 g at 4° C. The supernatant is recovered and filtered on a 60-µm sterile nylon mesh above a 50-mL tube. This last tube is centrifuged for 10 min at 400 g at 4° C. The cell pellet thus obtained is resuspended in a final volume of 50 mL of medium (HBSS; 2% FCS; 1% P/S). Washing is carried out by centrifugation for 10 min at 400 g at 4° C. The pellet is then taken up in a final volume of 120 mL in three 50-mL tubes of medium (HBSS; 2% FCS; 1% P/S) at room temperature.

The 120 mL of cell suspension is divided into 3 to be purified in a Ficoll-Hypaque gradient. 30 mL is carefully deposited per tube (4 tubes in total) containing 15 mL of Ficoll-Hypaque. The 4 tubes of Ficoll-Hypaque enriched with cell suspension are centrifuged at 1500 g without braking (deceleration 2, acceleration 5), for 30 minutes at room temperature. For each tube of Ficoll-Hypaque, an upper phase is obtained composed of cell debris, a ring composed of mononuclear cells positioned as an interphase between the cell debris and the Ficoll phase, and finally a lower phase composed of red blood cells. The 4 rings (20 mL/tubes) are recovered and divided into three 50-mL tubes and washed with a final volume of 50 mL of medium (HBSS; 2% FCS; 1% P/S) at 700 g for 10 min. The pellets of mononuclear cells obtained are pooled. The final pellet is washed with 50 mL of medium (HBSS; 2% FCS; 1% P/S) by centrifugation at 400 g for 10 min. The pellet is taken up in 5 mL of RPMI, 10% FCS, 1% P/S, $5.10^{-5}$M of beta-mercaptoethanol. The mononuclear cells are stored in ice; a proportion of the cells is used for counting and observation of viability with trypan blue (sample diluted to 1/100). Once counted, the cells are distributed in a 96-well plate at a rate of $3.10^5$ cells/well.

1.4.2—Isolation of the Lymph Node Cells

The popliteal and subiliac lymph nodes, situated near the injection site, are removed as quickly as possible after euthanasia of the animals and are transferred to a sterile sample tube containing culture medium (HBSS supplemented with 2% foetal calf serum (FCS) and 1% penicillin/streptomycin (P/S)). The sample tube containing the sample is stored in ice until it reaches the research laboratory.

Each lymph node is defatted using previously sterilized forceps, scissors or scalpel. The lymph node is then deposited on a sterile (autoclaved) nylon mesh measuring 3 cm×3 cm placed at the bottom of a sterile Petri dish containing 10 ml of medium (HBSS; 2% FCS; 1% P/S). The lymph node is crushed and comminuted using a piston of a 5-mL syringe to release the cells contained in the lymph node. The medium thus enriched with cells is filtered using a 60-µm sterile nylon mesh positioned above a 50-mL tube for recovering the medium enriched with filtered cells. These last steps are repeated twice as follows: 10 mL of medium is added to the remaining fragments of lymph nodes. The fragments of lymph nodes are crushed, comminuted and filtered as described above. The 50-mL tube for recovering the filtered cell-enriched medium is centrifuged at 1600 g for 15 min at 4° C. Washing is carried out with 50 mL of medium (HBSS; 2% FCS; 1% P/S) by centrifugation for 10 min at 400 g at 4° C. The pellet is taken up in 5 mL of RPMI, 10% FCS, 1% P/S, $5.10^{-5}$M of beta-mercaptoethanol. The pellet is stored in ice; a proportion of the cells is used for counting and observation of viability with trypan blue (sample diluted to 1/100). Once counted, the cells are distributed in a 96-well plate at a rate of $3.10^5$ cells/well.

1.5—Investigation of the Inflammatory Response Post-Immunostimulation 1.5.1—from the Spleen Cells Once the mononuclear cells of the spleen have been isolated by Ficoll Histopaque gradient and distributed in a 96-well plate, at a rate of $3.10^5$ cells per well, the latter are stimulated in vitro with 30 µg/ml of total parasite extract of the strain Toxo mic1-3 KO. To establish a positive control for the experiments, the cells are stimulated with concanavalin A. Conversely, to establish a negative control for the experiments, the cells are cultured in a medium without stimulant. The supernatants are taken after 24 hours post-stimulation in vitro.

The technique used for assay of IFNγ is an ELISA of the sandwich type on a 96-well plate. The antibody (anti-IFNγ) immobilized on a plate reacts specifically with the IFNγ present in the test sample. The quantity of antigen-antibody is measured in a second phase after it has reacted with an antibody of identical specificity coupled to an enzyme.

All the dilutions of the various reagents are prepared in 1×PBS, 0.05% Tween 20 and 1% BSA, except for the capture antibody, which is diluted in 1×PBS.

50 µL per well of capture antibody diluted to 1/500 (Mouse anti-bovine IFNg clone CC 330, Serotec MCA2112, Initial concentration: 1000 µg/mL) is deposited in an ELISA plate (ELISA plate Nunc maxisorp 442404) and then incubated overnight at 4° C. Three washings are carried out in 1×PBS buffer with the addition of 0.05% Tween 20 (PBS-T). The non-specific sites are saturated by incubating the plates for 1 hour at room temperature with 200 μL of a 1×PBS solution; 0.05% Tween 20, 1% BSA. Three washings are carried out in 1×PBS buffer with the addition of 0.05% Tween 20 (PBS-T).

The range is prepared as follows: 50 μL of the standard range of rBoIFNγ is deposited at different concentrations: 4 ng/mL, 2 ng/mL, 1 ng/mL, 0.5 ng/mL, 0.25 ng/mL, 0.125 ng/mL, 0.0625 ng/mL, 0.03125 ng/mL, 0.015 ng/mL. In parallel, the samples (supernatant of stimulated mononuclear cells) are deposited at a rate of 50 μL per well. The samples and the standard range are incubated for 1 h at room temperature. 4 washings are carried out in 1×PBS buffer with the addition of 0.05% Tween 20 (PBS-T).

50 μL of biotinylated detection antibodies (Mouse anti-bovine IFNg: biotin clone CC 302 (Serotec MCA1783B) Initial concentration: 500 μg/ml) diluted to 1/500 is deposited per well, for an incubation time of one hour at room temperature. A series of 4 washings is carried out in 1×PBS buffer with the addition of 0.05% Tween 20 (PBS-T).

IFNγ is detected by a biotin-ExtrAvidine® affinity reaction followed by a colorimetric reaction between peroxidase and its substrate: 50 μL of a solution of modified avidin coupled to a peroxidase (ExtrAvidine-Peroxidase Conjugate® (Sigma E2886)) diluted to 1/2000th is deposited per well and incubated for 20 minutes at room temperature. A series of 4 washings is carried out in 1×PBS buffer with the addition of 0.05% Tween 20 (PBS-T). Detection is carried out using 50 μL/well of peroxidase substrate originating from a solution A and B mixed volume for volume (TMB Peroxidase substrate Eurobio KPL solution A 50-76-01 and solution B 50-65-00). The substrate solution is incubated for 15 minutes at room temperature. 50 μL of stopping solution (phosphoric acid 1M Sigma 43,080-1, CAS 7664-38-2) is added per well under a fume hood.

The plates are read at wavelength $\lambda=450$ nm. The standard curve is determined by the following function: OD value as a function of the concentration of the recombinant IFNγ. The OD values of the samples tested are converted to concentration using the standard curve. To be taken into account, the samples must give ODs located on the linear portion of the standard curve.

1.5.2—from the Lymph Node Cells

The lymph node cells distributed in a 96-well plate at a rate of $3.10^5$ cells per well are cultured without any stimulant in order to detect expression of the cytokines ex-vivo. The supernatants of the lymph node cells are taken after 24 hours. IFNγ is assayed by the ELISA technique as described above.

2—Results 2.1—Experimental Procedure

After ingestion of colostrum, the lambs are separated from their mothers and are fed with a lamb feeder bucket. The 4 lambs in batch A were immunostimulated with $10^6$ tachyzoites of the strain Toxo mic1-3 KO, freshly produced. After inoculation with the strain Toxo mic1-3 KO, no severe clinical sign was found and the lambs immunostimulated with the strain Toxo mic1-3 KO have a weight curve similar to the weight gain of the control lambs (FIG. 14).

The lambs from batch A and from batch B were euthanased 15 days after immunostimulation.

2.2—Investigation of the Inflammatory Response Post-Immunostimulation

The results of the assays of the IFN-γ produced from splenocytes restimulated with total extract of *T. gondii* and from the cells of the subiliac and popliteal lymph nodes are presented in FIGS. 15 and 16.

The lambs of the control batch (1423 and 1428) did not develop an inflammatory response (IFN-γ secretion), either in the spleen, or in the subiliac and popliteal lymph nodes.

In contrast, 15 days after immunostimulation, the cells of the subiliac lymph nodes of 3 lambs out of 4 produce IFN-γ. These lymph nodes are situated downstream of the injection site, in contrast to the popliteal lymph nodes, situated upstream and in which no production of IFN-γ is detected.

The inflammatory response of the lambs immunostimulated with the strain Toxo mic1-3 KO is confirmed after restimulation of the splenocytes with total parasite extract of the strain Toxo mic1-3 KO, since production of IFN-γ is induced for the 4 lambs. The splenocytes are also stimulated with concanavalin A, a protein of the lectin family, known to be a polyclonal activator of the T lymphocytes, which serves as positive control of stimulation of the immune system cells.

Example 9

Protection Against Cryptosporidiosis of Lambs Immunostimulated Subcutaneously with the Mutant Toxo Mic1-3 KO 1—Experimental Protocol 1.1—Animals Immunostimulation is carried out on 1-day-old neonate lambs After ingestion of colostrum, the lambs were isolated from their mothers in a sealed sheep house (INRA—Nouzilly) in order to limit the risks of natural contamination.

At the end of the experiments, the lambs were anaesthetized by electronarcosis and then euthanased to collect the various organs. Only the animal keepers and the experimenters, equipped with clothing for use inside the animal house, may enter the buildings, in order to prevent contamination of the environment, and they only leave the sealed zone after showering.

1.2—*Cryptosporidium parvum*

Oocysts of *Cryptosporidium parvum* are obtained from excrement of calves infected with $10^7$ *C. parvum* oocysts. The stool undergoes various treatments until a suspension of sterile, purified parasites is obtained, suitable for use in cell culture. Throughout the treatment, the oocysts are manipulated at 4° C. to prevent excystation of the oocysts.

Briefly, after recovery of the stool, the latter is diluted in fresh water and then passed through a 100-μm filter and centrifuged at 1900 g for 10 minutes at 4° C. The pellets obtained, containing the oocysts, are taken up in 2% potassium dichromate solution (Prolabo, ref. 26 776 290, CAS 7778-50-9), and are then washed twice with cold water by centrifugation at 1900 g for 10 minutes at 4° C. to remove the potassium dichromate. After washing, the pellet of coccidia is taken up in a mixture of water and ether (ethyl ether, Carlo Erba, CAS No. 60-29-7) diluted to 1/5, then centrifuged again at 1900 g for 10 minutes at 4° C. The upper phases containing the fats and the ether are removed and the pellet is recovered and taken up in cold water after passing through a 20-μm filter. Two to three millilitres of the suspension of parasites obtained is deposited on a glucose gradient prepared from Sheather solution (sucrose 500 g, water 320 ml, 0.2 g of sodium azide (Prolabo, CAS 26628-22-8)). Two rings of oocysts are formed after centrifugation of the glucose gradient at 2000 g for 20 minutes at 4° C. The two rings are recovered and washed several times in cold water. The purified oocysts are then sterilized. After centrifugation at 1900 g for 10 minutes at 4° C., the pellet of oocysts is incubated for 15 minutes in a solution of bleach (sodium hypochlorite (Sigma 239305-500ML Titre: 4.5% of active chlorine)) diluted to 10% in demineralized water, then washed 3 times in sterile 1×PBS (diluted from a solution of PBS 10×: sodium chloride, NaCl 80 g/litre water; potassium chloride, KCl 2 g/litre; potassium dihydrogen phosphate, $KH_2PO_4$: 2 g/litre; disodium hydrogen phosphate, $Na_2HPO_4$, 12 $H_2O$: 29 g/litre). The purified and sterilized oocysts are counted on a slide (5 μL of solution of oocysts and 495 μL of malachite green), adjusted to a concentration of $2 \times 10^8$ oocysts/mL, divided into aliquots in 1.5-mL tubes and stored at 4° C.

1.3—Strain Toxo mic1-3 KO

The mutant strain of *Toxoplasma gondii*, in which the genes coding for the proteins TgMIC1 and TgMIC3 have been knocked out (called strain Toxo mic1-3 KO) is maintained by successive passages on a human foreskin fibroblast (HFF) line cultured in DMEM medium supplemented with 10% of foetal calf serum (FCS), 2 mM of glutamine, 50 U/mL of penicillin and 50 μg/mL of streptomycin.

1.4—Immunostimulation

Two batches of 1-day-old male lambs were treated as follows:

8 lambs (batch A) served as unvaccinated control batch, 8 lambs (batch B) received the mutant Toxo mic1-3 KO.

On D1, the lambs in batch B received $10^6$ tachyzoites of the strain Toxo mic1-3 KO by intraperitoneal route.

On D7 post-infection, the lambs in batch A and in batch B were challenged with $5.10^6$ oocysts of *Cryptosporidium parvum* and the lambs were sacrificed on D31.

1.5—Investigation of Protection

To analyse the protection generated by immunostimulation with the strain Toxo mic1-3 KO, 3 parameters were studied:

Survival—Mortality

After challenge with *Cryptosporidium parvum*, the lambs were monitored daily for 25 days (until D31).

Weight gain:

The lambs in batch A and in batch B were weighed every 2-3 days to evaluate their weight gain.

Excretion of oocysts:

The faeces of the lambs were recovered daily from D9 to D22 and were stored at +4° C. After weighing, 26 mg of faecal matter is diluted in 750 μL of water. 4 mL of sucrose solution is added. After homogenization, 20 μL is deposited on a Thoma slide and the oocysts are counted. The number of oocysts excreted is then calculated with the following formula: N=n×10 000×20 (N: number of oocysts per g or per ml, n=number of oocysts counted on the cell, 20=dilution 1/4×1/5).

2—Results 2.1—Experimental Procedure

After ingestion of colostrum, the lambs are separated from their mother and are fed with a lamb feeder bucket. 3 lambs from batch B and 1 lamb from batch A were unable to feed properly and were euthanased. Since euthanasia took place before the infectious challenge, these animals were statistically removed from the protocol.

2.1—Investigation of protection

Survival—Mortality

Following infection with *C. parvum*, four lambs essentially of the control batch (batch A) were euthanased, in contrast to the immunostimulated batch (batch B), in which no lamb died following infection with *C. parvum* (FIG. 17).

Weight gain

The daily weight gain (DAG, daily average gain) of the lambs in batch A and in batch B is presented in FIG. 18. A significantly lower DAG is found for batch A challenged only with *C. parvum* than for batch B immunostimulated with the strain Toxo mic1-3 KO and then challenged with *C. parvum*.

Excretion of oocysts

Analysis of the parasitic load in the excrement of the lambs shows a shift of the excretion peak of one day for the batch immunostimulated with the strain Toxo mic1-3 KO, with a 70% drop of the mean excretion peak observed at 5 days post-infection with *C. parvum* compared to the mean excretion peak for the control batch challenged only with *C. parvum* observed at 4 days post-infection with *C. parvum* (FIG. 19).

The invention claimed is:

1. Method for the prevention or the treatment, in a neonate mammal, of a pathology associated with an apicomplexan of the family of Cryptosporidiidae, comprising a step of administration, to said neonate mammal, of strains of Sarcocystidae selected from *Toxoplasma* spp or *Neospora* spp isolated from their natural environment and having an immunostimulant effect.

2. Method for the prevention or the treatment, in a neonate mammal, of a pathology associated with an apicomplexan of the family of Cryptosporidiidae according to claim 1, in which said mammal is a human being or an animal.

3. Method for the prevention or the treatment, in a neonate mammal, of a pathology associated with an apicomplexan of the family of Cryptosporidiidae according to claim 2, in which said animal belongs to the group comprising or constituted by ovines, caprines, porcines, bovines, equines, camelids, canids or felids.

4. Method for the prevention or the treatment, in a neonate mammal, of a pathology associated with an apicomplexan of the family of Cryptosporidiidae according to claim 1, in which said strains of *Toxoplasma* spp or of *Neospora* spp have at least an adhesin MIC-1 and/or an adhesin MIC-3 inactivated by a genetic modification relating to at least one of the mic-1 and/or mic-3 genes.

5. Method for the prevention or the treatment, in a neonate mammal, of a pathology associated with an apicomplexan of the family of Cryptosporidiidae according to claim 1, in which said strains of *Toxoplasma* spp or of *Neospora* spp have the two adhesins MIC-1 and MIC-3 inactivated by a genetic modification relating to the two mic-1 and mic-3 genes.

6. Method for the prevention or the treatment, in a neonate mammal, of a pathology associated with an apicomplexan of the family of Cryptosporidiidae according to claim 4, in which the strains of *Toxoplasma* spp or of *Neospora* spp are respectively *Toxoplasma gondii* or *Neospora caninum*.

7. Method for the prevention or the treatment, in a neonate mammal, of a pathology associated with an apicomplexan of the family of Cryptosporidiidae according to claim 1, in which the immunostimulant effect of said strains leads to the secretion of interleukin-12 (IL-12) and then of interferon-γ (IFN-γ).

8. Method for the prevention or the treatment, in a neonate mammal, of a pathology associated with an apicomplexan of the family of Cryptosporidiidae according to claim 7, in which the secretion of interleukin-12 (IL-12) and of interferon-γ (IFN-γ) begins between 3 and 9 days after using said strains of *Toxoplasma* spp or of *Neospora* spp as immunostimulant.

9. Method for the prevention or the treatment, in a neonate mammal, of a pathology associated with an apicomplexan of the family of Cryptosporidiidae according to claim 1, in which said pathology associated with an apicomplexan of the family Cryptosporidiidae is cryptosporidiosis.

10. Method for the prevention or the treatment, in a neonate mammal, of a pathology associated with an apicomplexan of the family of Cryptosporidiidae according to claim 9, in which the apicomplexan of the family Cryptosporidiidae responsible for the cryptosporidiosis is at least one apicomplexan selected from the group constituted by *Cryptosporidium parvum, Cryptosporidium bovis, Cryptosporidium andersoni, Cryptosporidium ryanae, Cryptosporidium muris, Cryptosporidium ubiquitum, Cryptosporidium hominis, Cryptosporidium canis, Cryptosporidium felis, Cryptosporidium baileyi, Cryptosporidium meleagridis* or *Cryptosporidium xiaoi*.

11. Method for the prevention or the treatment, in a neonate mammal, of a pathology associated with an apicomplexan of the family of Cryptosporidiidae according to claim 6, comprising a step of administration, to said neonate mammal, of strains of *Toxoplasma gondii* or *Neospora caninum* isolated from their natural environment and having an immunostimulant effect, said strains of *Toxoplasma gondii* or of *Neospora caninum* having the two adhesins MIC-1 and MIC-3 inactivated by a genetic modification relating to the two mic-1 and mic-3 genes, in which said pathology associated with an apicomplexan of the family Cryptosporidiidae is cryptosporidiosis.

12. Method for the prevention or the treatment, in a neonate mammal, of a pathology associated with an apicomplexan of the family of Cryptosporidiidae according to claim 6, comprising a step of administration, to said neonate mammal, of strains of *Toxoplasma gondii* or *Neospora caninum* isolated from their natural environment and having an immunostimulant effect, said strains of *Toxoplasma gondii* or of *Neospora caninum* having the two adhesins MIC-1 and MIC-3 inactivated by a genetic modification relating to the two mic-1 and mic-3 genes, in which said strains of *Toxoplasma gondii* or of *Neospora caninum* are administered to the mammal at a rate from 20 to $10^9$ tachyzoites.

13. Method for the prevention or the treatment, in a neonate mammal, of a pathology associated with an apicomplexan of the family of Cryptosporidiidae according to claim 1, in which said strains are in a galenic form comprising or constituted by liquid suspensions, solid or liquid dispersions, powders, pastes or lyophilizates.

14. Method for the prevention or the treatment, in a neonate mammal, of a pathology associated with an apicomplexan of the family of Cryptosporidiidae according to claim 1, in which said strains are associated with at least one other antigen, or at least one adjuvant, or at least one stabilizer, or at least one preservative or a mixture of at least two of said products for increasing the immune response of said mammal.

15. Method for the prevention or the treatment, in a neonate mammal, of a pathology associated with an apicomplexan of the family of Cryptosporidiidae according to claim 5, in which the strains of *Toxoplasma* spp or of *Neospora* spp are respectively *Toxoplasma gondii* or *Neospora caninum*.

* * * * *